United States Patent [19]

Kudryk et al.

[11] Patent Number: 4,851,334
[45] Date of Patent: * Jul. 25, 1989

[54] MONOCLONAL ANTIBODIES SPECIFIC TO IN VIVO FRAGMENTS DERIVED FROM HUMAN FIBRINOGEN, HUMAN FIBRIN I OR HUMAN FIBRIN II

[75] Inventors: Bohdan J. Kudryk, Little Ferry, N.J.; Michael E. Wiebe, Stamford, Conn.

[73] Assignee: The New York Blood Center, Inc., New York, N.Y.

[*] Notice: The portion of the term of this patent subsequent to Feb. 2, 2005 has been disclaimed.

[21] Appl. No.: 84,002

[22] Filed: Aug. 10, 1987

Related U.S. Application Data

[63] Continuation of Ser. No. 567,462, Jan. 3, 1984, Pat. No. 4,722,903, which is a continuation-in-part of Ser. No. 550,836, Nov. 11, 1983, abandoned.

[51] Int. Cl.$^4$ .................. C07K 15/04; A61K 39/395; G01N 33/577; C12N 5/10
[52] U.S. Cl. ....................................... 435/7; 530/387; 530/388; 435/68; 435/70; 435/172.2; 435/240.27; 435/188; 424/1.1; 424/85.8; 436/518; 436/542; 436/540; 436/537; 436/543; 436/544; 436/545; 935/95; 935/104; 935/108; 935/110
[58] Field of Search .................. 530/387, 388; 435/68, 435/70, 172.2, 240.27, 188.7; 424/1.1, 85; 436/518, 542–545, 540, 537; 935/95, 102–104, 106–108, 110

[56] References Cited

U.S. PATENT DOCUMENTS

| | | | |
|---|---|---|---|
| 4,443,427 | 4/1984 | Reinherz | 424/1.1 |
| 4,443,549 | 4/1984 | Sadowski | 436/548 |
| 4,465,776 | 8/1984 | Cidlowski | 436/504 |
| 4,468,346 | 8/1984 | Paul | 435/7 |
| 4,487,829 | 12/1984 | Sharp | 435/7 |
| 4,487,833 | 12/1984 | Donahoe | 435/172.2 |
| 4,722,903 | 2/1988 | Kudryk et al. | 435/7 |

OTHER PUBLICATIONS

Biological Absts, vol. 78–1984–No. 24799–B. Kudryk et al., "A Monoclonal Antibody—Fibrin".
Biological Absts., vol. 78–1984–No. 8595: B. Kudryk et al., "Specifity of a Monoclonal—Fibrin".
Biological Absts, vol. 77, 1984–No. 80886; D. B. Rylatt et al., "An Immunoassay for Human—Antibodies".
Science, vol. 222 -Dec. 9, 1983, pp. 112-1132; K. Y. Hui et al., "Monoclonal Antibodies to a Synethetic—Fibrinogen".
Chemical Absts., vol. 95, 1981, p. 573; Abs. No. 78340s, Col. Ohio–S. J. Kennel et al., "Monoclonal Antibodies from Rats Fibrinogen".
Biological Absts., vol. 76, 1983, Abstract No. 62261; B. P. R. Sola et al., "Isolation and Characterization—Origin".
Biological Absts., vol. 76, 1983, Abstract No. 69855; S. J. Kennel et al., "Solid–Phase Radioimmunoassay—Antibody".

(List continued on next page.)

Primary Examiner—Margaret Moskowitz
Attorney, Agent, or Firm—Sprung Horn Kramer & Woods

[57] ABSTRACT

Hybridoma for production of monoclonal antibody to an antigen found on the peptide fragment of the Bβ chain of human fibrinogen or fibrin I containing amino acid residues 1–42. The hybridoma is formed by fusing an animal myeloma cell, e.g., mouse myeloma cell, with a splenocyte from an animal, e.g., a mouse, immunized with an $NH_2$-terminal of human fibrinogen or fibrin I. Hybridoma for production of monoclonal antibody to an antigen found on the peptide fragment of the Bβ chain of human fibrin II containing amino acid residues 15–42. The hybridoma is formed by fusing an animal, e.g., mouse myeloma cell with a splenocyte from an animal, e.g., mouse, immunized with a $NH_2$-terminal of human fibrin II. Diagnostic and therapeutic uses of the monoclonal antibodies are also disclosed.

41 Claims, 8 Drawing Sheets

OTHER PUBLICATIONS

Biological Absts., vol. 77, 1984, Abstract No. 40751; M. J. I. H. Elms Elms et al., "Measurement of Crosslinked Fibrin—Antibodies".
Blomback et al., *Nature,* Lond., 257, 501–505, 1978.
Kernoff and McNicol, Br Med. Bull., 33, 239–244, 1977.
Collen, *Thromb. Haemostas.,* 43, 77–89, 1980.
Mosesson et al., *J. Biol. Chem.,* 247, 5210–5219, 1972.
Takagi and Doolittle *Biochemistry,* 14, 940–946, 1975.
Plow and Edington, *J. Clin. Invest.,* 52, 273–282, 1973 and in *J. Biol. Chem.,* 250, 3386–3392, 1975.
Canfield et al., *Biochemistry,* 15, 1203–1208, 1976.
Wilner et al., *Biochemistry,* 15, 1209–1213, 1976.
Bilezikian et al., *J. Clin. Invest.,* 56, 438–445, 1975.
Kohler and Milstein, *Nature,* 256, 495–497, 1975.
C. J. Barnstable et al., *Cell,* 14, 9–20, May, 1978.
F. Melchers, M. Potter and N. Warner, eds., Current Topics in *Microbiology and Immunology,* 81–"Lymphocyte Hybridomas", Springer-Verlag, 1978.
P. Parham and W. F. Bodmer, *Nature,* 276, 397–399, Nov., 1978.
D. M. Wier, ed., *Handbook of Experimental Immunology,* Third Edition, 2, Blackwell, 1978, Chapter 25; and *Chemical and Engineering News,* Jan. 1, 1979, 15–17.
Blomback et al., *Nature,* 218, 130–134, 1968.
Kudryk et al., *J. Biol. Chem.,* 249, 3322–3325, 1974.
Laurent & Blomback, *Acta Chem. Scand.,* 12, 1875–1877, 1958.
Qureshi et al., *Thromb. Res.,* 6, 357–375, 1975.
Kudryk et al., *Thromb. Res.,* 25, 277–291, 1982.
Nossel et al. *J. Clin. Invest.,* 64, 1371–1378, 1979.
Nossel, *Nature,* Lond., 291, 165–167, 1981.
Matsueda et al., *Science,* 222, 1129–1132, 1983.
Koehn and Canfield, *Analyt. Biochem.,* 116, 349–356, 1981.
Engvall, E., *In Methods in Enzymology,* 70, Part A, 419–439, 1980.
Blomback et al., *J. Biol. Chem.,* 248, 5806–5820, 1973.
Blomback et al., *J. Biol. Chem.,* 241, 1496–1512, 1972.
Gardlund et al., *Thromb. Res.,* 1, 371–388, 1972.
Hessel et al., *Eur. J. Biochem.,* 98, 521–534, 1979.
Hessel, *Doctoral Thesis,* Chem. Dept., Karolinska Institutet, Stockholm, Sweden, 1975.
Kohler and Milstein, *Eur. J. Immun.,* 6, 511–519, 1976.
Littlefield, *Science,* 145, 709–710, 1964.
Blomback & Yamashina, 1958.
Wilhelmsson et al., *Clin Nephrol.,* 15, 252–258, 1981.
Hayne and Sherman, *Am. J. Path.,* 71, 219–236, 1973.
Iio et al., *J. Lab. Clin. Med.,* 87, 934–947, 1976.
Rosebrough, S. F. et al., Radiology 156:515–517 (1985).
Pacella, B. L. et al., Molecular Immunology, 20(5): 521–527 (1983).
Matsueda, G. R. et al., Proceedings: Amer. Sympos. Rept., Tucson, U.S., Meeting Date 5–1983.
Kudryk, B. et al., Molecular Immunology 21(1):89–94 (1984).
Kudryk, B. et al., Molecular Immunology 20(11): 1191–1200 (1983).
Wade, N., Science, vol. 215, pp. 1073–1075 (2–1982).
Dixon, B., Bioltechnology, vol. 2(1), pp. 26, 93 (1–1984).
Bouchieua, C. et al., Protides of the Biol. Fluids, pp. 399–402 (1983).
Castellino, F. J. et al., Haemostais, vol. 14(1), p. 44 (1984).
Matsueda, G. R. et al., Fed. Amer. Soc. for Experimental Biology, vol. 42(7), p. 1992 (1983).
Sobel, J. H. et al., Thromb. Haemostasis, vol. 46(1), p. 240 (1981).
Sobel, J. H. et al., Thromb. Haemostasis, vol. 50(1), p. 265 (1983).
Soria, J. et al., Annals of the N.Y. Acad. Sci., (1983), pp. 665–666, Mosesson, M. W. et al., eds. Meeting Date (6–1982).
Ehrlich, P. H. et al., Biochemistry, vol. 22, pp. 4184–4192 (1983).
Joshua, D. E. et al., Pathology, vol. 16(3), p. 357 (1984).
Joshua, D. et al., Thromb. Haemostasis, vol. 50(1), pp. 307 (1983).
Sobel, J. H. et al., Biochemistry, vol. 22, pp. 4175–4183 (1983).

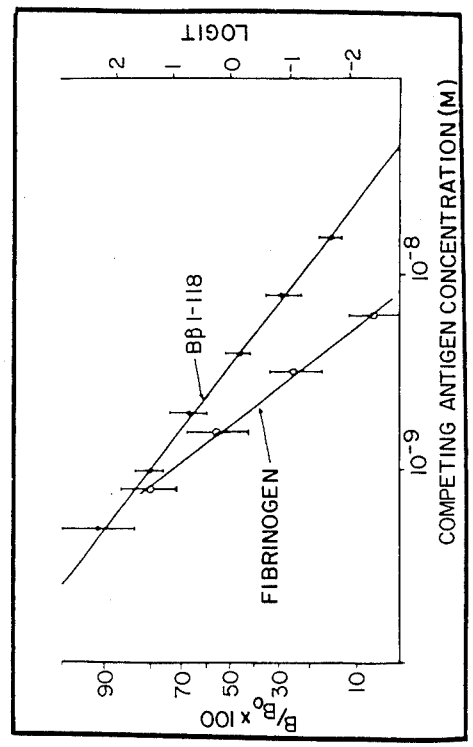
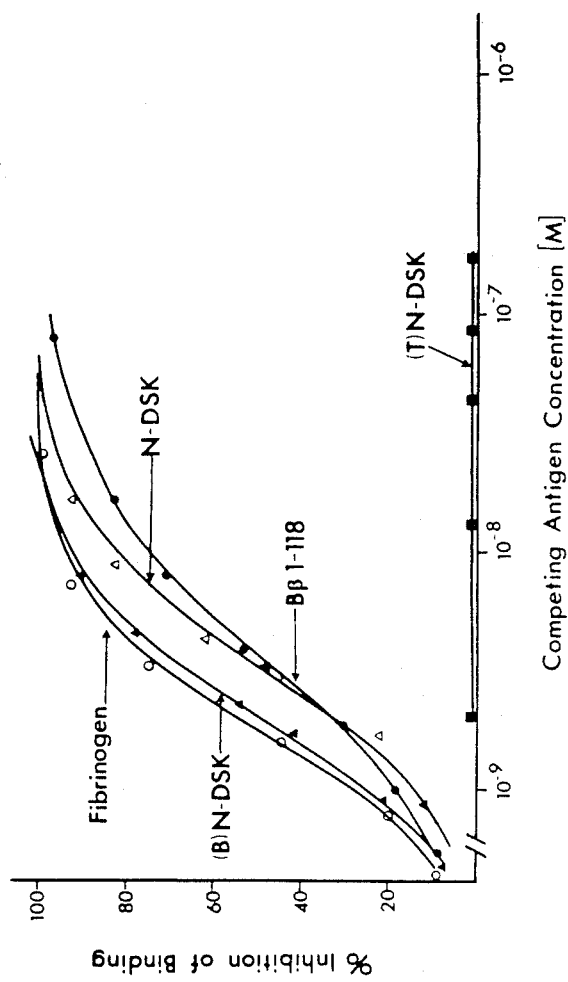
FIG. 4

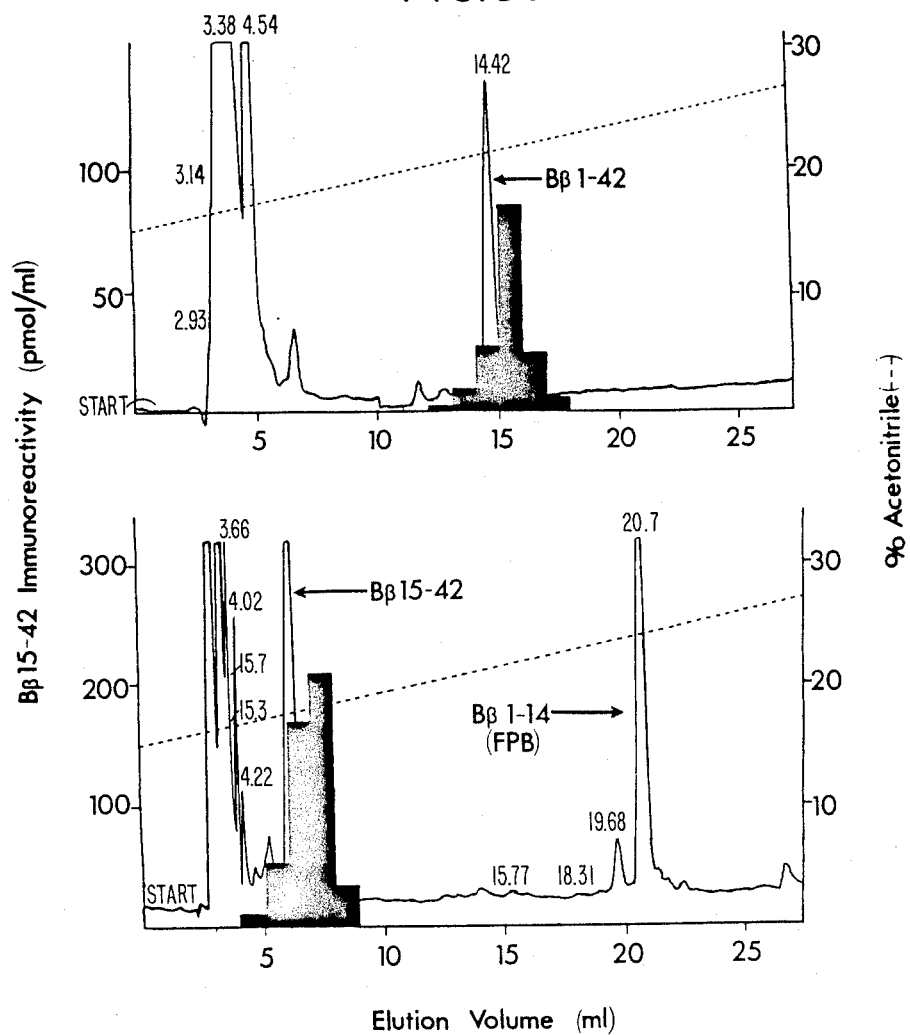

MONOCLONAL ANTIBODIES SPECIFIC TO IN VIVO FRAGMENTS DERIVED FROM HUMAN FIBRINOGEN, HUMAN FIBRIN I OR HUMAN FIBRIN II

CROSS-REFERENCE TO RELATED APPLICATION

This application--continuation of application ser. No. 567,462, filed Jan. 3, 1984, U.S. Pat. 4,722,903 issued Feb. 2, 1988, which in turn-is a continuation-in-part of Patent Application Ser. No. 550,836 filed Nov. 11, 1983 now abandoned, entitled "Monoclonal Antibody Specific to An In Vivo Fragment Derived From Fibrinogen at Fibrin I".

BACKGROUND OF THE INVENTION

This invention relates to new hydridomas (hybrid cell lines), namely ATCC HB 8418 and ATCC HB 8426, filed Nov. 9, 1983 and Nov. 16, 1983, respectively. More specifically, this invention concerns the production of monoclonal antibodies from each of such new hybridomas such antibodies specific to in vivo fragments derived from fibrinogen, and to diagnostic and therapeutic methods and compositions employing these antibodies.

Fibrinogen is a large ($M_r$340,000) dimeric molecule composed of three non-identical polypeptide chains. The fibrinogen-fibrin transition involves the sequential release of fibrinopeptides. In this two-stage thrombin-mediated process, fibrin I is the initial product and it is formed following the release of FPA [fibrinopeptide A (A$\alpha$ 1-16)]. Fibrin II, a more compact structure, results upon the release of FPB [fibrinopeptide B (B$\beta$ 1-14)] (Blombäck et al., Nature, Lond., 257, 501-505, 1978). Dissolution of fibrin—be it fibrin I or II—deposits is required in order to restore vascular integrity. This is achieved principally via the plasmin pathway (see Kernoff and McNicol, Br. Med. Bull., 33, 239-244, 1977 and Collen, Thromb. Haemostos., 43, 77-89, 1980). One of the early plasmin degradation products of fibrinogen or fibrin is derived from the $NH_2$-terminal portion of the B$\beta$ chain. The bond B$\beta$ 42 Arg-43 Ala is particularly susceptible to plasmin (Mosesson et al., J. Biol. Chem., 247, 5210-5219, 1972; Takagi and Doolittle, Biochemistry, 14, 940-946, 1975). The nature of the B$\beta$ chain peptide released by plasmin depends upon the available substrate. Cleavage of fibrinogen or fibrin I will result in the FPB containing peptide B$\beta$ 1-42. The latter, of course, cannot be generated in plasmin proteolysis of fibrin II, which results in the release of peptide B$\beta$ 15-42.

Identification and quantitation of thrombin and plasmin degradation products of fibrinogen and fibrin may serve as valuable diagnostic tests. During the past decade, a number of immunoassays have been developed for this purpose. Antisera prepared by conventional immunization have been used in most of these assays. Since such antisera contain antibodies of varying titer, affinity and specificity, a number of problems have been encountered. For example, antibodies to cleavage-associated neo-antigens found on certain fragments of fibrinogen and fibrin have generally been present in extremely low titer (Plow and Edgington, J. Clin. Invest., 52, 273-282, 1983; J. Biol. Chem., 250, 3386-3392, 1975). Regarding cross-reactivity, most antisera react with intact fibrinogen and, therefore, plasma samples require a processing step(s) in order to selectively remove it. Significant differences in immunoreactivity have been observed for antisera prepared to both FPA and FPB (Canfield et al., Biochemistry, 15, 1203-1208, 1976; Wilner et al., Biochemistry, 15, 1209-1213, 1976; Bilezikian et al., J. Clin. Invest., 56, 438-445, 1975). Some of these antisera show limited cross-reactivity with peptides that are only a few amino acid residues longer than free FPA or FPB.

The development of the hybridoma technique by Köhler and Milstein, Nature, 256, 495-497, 1975, may allow refinement of most of the immunoassays dealing with fibrinogen or fibrin degradation products.

The fusion of mouse myeloma cells to spleen cells from immunized mice by Köhler and Milstein demonstrated for the first time that it was possible to obtain a continuous cell line making monoclonal antibody. Subsequently, much effort has been directed to the production of various hybrid cells (hybridomas) and to the use of the antibody made by these hybridomas. See, for example, F. Melchers, M. Potter, and N. Warner, eds., Current Topics in Microbiology and Immunology, 81--"-Lymphocyte Hybridomas", Springer-Verlag, 1978, and the references contained therein; C. J. Barnstable, et al., Cell, 14, 9-20, May, 1978; P. Parham and W. F. Bodmer, Nature, 276, 397-399 November, 1978; D. M. Wier, ed., Handbook of Experimental Immunology, Third Edition, 2, Blackwell, 1978, Chapter 25; and Chemical and Engineering News., Jan. 1, 1979, 15-17. These references indicate the problems inherent in attempting to produce monoclonal antibodies from hybridomas. While the general technique is well understood, there are many difficulties and variations in each specific case.

In fact, there is no assurance, prior to attempting to prepare a given hybridoma, that the desired hybridoma will be obtained, that it will produce antibody if obtained, or that the antibody so produced will have the desired specificity. The degree of success is influenced principally by the type of antigen employed and the selection technique used for isolating the desired hybridoma.

Prior research had shown that cleavage of fibrinogen in vitro with CNBr results in the release of a major $NH_2$-terminal fragment, the so-called N-DSK (Blombäck et al., Nature, 218, 130-134, 1968). The N-DSK portion of fibrinogen contains binding or polymerization domains which are exposed as a consequence of enzyme activation and which are operative in the fibrinogen to fibrin transition (Kudryk et al., J. Biol. Chem., 249, 3322-3325, 1974). The enzyme thrombin can cleave FPA an FPB from fibrinogen, and release of both peptides results in the formation of fibrin II. In contrast to thrombin, the snake venom enzyme Bathroxobin can release only FPA from fibrinogen (Laurent & Blombäck, Acta Chem. Scand., 12, 1875-1877, 1958), a process which leads to the formation of a type of fibrin which has been termed fibrin I. Since the $NH_2$-terminal ends of fibrinogen and N-DSK are identical, different N-DSK species can be obtained from thrombin and Batroxobin induced fibrin gels.

In hope of identifying neoepitopes, Qureshi et al., Thromb. Res., 6, 357-374, 1975, prepared rabbit antisera to human (T)N-DSK. Despite the fact that high titer sera were obtained, these investigators could not demonstrate any immunochemical differences between N-DSK and (T)N-DSK.

In 1982, Kudryk et al., developed a radioimmunoassay which could be used to measure the plasma levels of peptides containing the Bβ 15-42 sequence derived from fibrinogen or fibrin (Kudryk et al., Thromb. Res., 25, 277-291, 1982). Since these peptides arise as a consequence of in vivo plasmin digestion, it was proposed that the assay could give important information in clinical studies on disease states where thrombosis was imminent or manifest. However, the assay could not distinguish between peptides containing extensions at either the NH$_2$- or COOH-terminal end of Bβ 15-42 and, therefore, only the total Bβ 15-42 immunoreactivity could be measured.

Nossel et al., J. Clin. Invest., 64, 1371-1378, 1979, have identified Bβ 1-42 in clinical blood samples and suggested that it arises from plasmin proteolysis of the so-called fibrin I. A second type of fibrin is also formed in vivo. By definition, fibrin II lacks both FPA and FPB and, therefore, its dissolution by plasmin cannot generate Bβ 1-42 (See FIG. 8 herein). Nossel (*Nature*, Lond., 291, 165-167, 1981) has suggested that fibrin I is the pivotal substrate in fibrinogen proteolysis *in vivo* and that fibrin II is more likely to result in occlusive thrombosis (see FIG. 8 herein). Since occlusive thrombosis imperils a patient's life, the incipiency of thrombosis must be detected. The degradation of fibrinogen in vivo results in products which cause thrombosis, depending on the prevalent enzymatic reactions occurring during fibrinogen proteolysis. Problems have existed in that it has been difficult to determine in any reliable manner, whether the fibrin I polymer which results from thrombin activation of fibrinogen is, in turn, activated by thrombin or plasmin. If activated primarily by plasmin, split products, including a fragment of the Bβ chain of fibrin I containing amino acid residues 1-42, are produced. If the latter is the predominant pathway, occlusive thrombosis does not occur. If fibrin I polymer is, instead, further activated by thrombin, fibrin II is formed and this is often accompanied by thrombosis.

In light of the above it has become very desirable to determine which biochemical route the fibrin I molecule is taking. One approach for doing this is to identify the molecular nature of the Bβ chain peptides in clinical samples. For example, confirmation of the predominance of intact Bβ 1-42 in a patient's blood plasma, with a coupled negative indication of peptide fragments of the Bβ chain containing amino acid residues 1-14 and 15-42, would strongly suggest plasmin protolysis of fibrin I. On the other hand, the reverse finding would indicate that fibrin I had been further degraded to yield fibrin II. As mentioned above, plasmin degradation of fibrin II can never yield Bβ 1-42.

Matsueda et al., Science, 222, 1129-1132, 1983, developed three monoclonal antibodies that bind to human fibrin from hybridomas prepared from fusion of cells of a Sp 2/O myeloma cell line and spleen cells from a female BALB/c mouse immunized with a complex consisting of a synthetic heptapeptide of the amino terminus of the Bβ chain of human fibrin, a cysteine residue placed at the heptapeptide's carboxy terminus, and MB-KLH (maleimidobenzoylated keyhole limpet hemocyanin). One of the monoclonal antibodies cross-reacted with fibrin from species other than human, e.g., rabbit fibrin.

DEFINITIONS

FPA : fibrinopeptide A (Aα 1-16)
FPB : fibrinopeptide B (Bβ 1-14)
Fibrin I : fibrin lacking FPA prepared by clotting fibrinogen with the snake venom enzyme Batroxobin
Fibrin II : the fully formed fibrin (lacking FPA and FPB) resulting from thrombin digestion of fibrinogen
HPLC : high-performance liquid chromatography
Hybridoma ATCC HB 8418: Mouse lymphocyte hybridoma given designation HB 8418 by American Type Culture Collection, 12301 Parklawn Drive, Rockville, Md. 20852 hereinafter, "ATCC", deposited on Nov. 9, 1983 (Depositor's Reference: 1-8C6)
Hybridoma ATCC HB 8426 : Mouse lymphocyte hybridoma given designation HB 8426 by ATCC, deposited on Nov. 16, 1983 (Depositor's Reference: T2G1s)
Monospecific antibody : an antibody that combines with a single antigen. A mono-specific antibody which is mono-specific to a single antigenic determinant combines only with that antigenic determinant (epitope).
Hetero-molecular antibody : an antibody that contains multiple different molecular forms of the same antibody.
Homo-molecular antibody : an antibody that contains only a single molecular form, i.e., each antibody molecule is the same as each other antibody molecule.
Monoclonal antibody : an antibody derived from a single cell line genetically identical and producing a home-molecular antibody.
MAb/1-8C6 : Monoclonal Antibody 1-8C6, the IgG fraction from spent medium of mass culture of the hybridoma clone, designated ATCC HB 8418
MAb/T2G1s : Monoclonal Antibody T2G1s, the IgG fraction from spent medium of mass culture of the hybridoma clone, designated ATCC HB 8426
N-DSK : NH$_2$-terminal portion of human fibrinogen obtained by CNBr cleavage with molecular formula (Aα 1-51, Bβ 1-118, γ 1-78)$_2$ with mol. wt. 58,000 (mol. wt. determined by gel electrophoresis)
(B)N-DSK : CNBr fragment obtained from human fibrin which had been prepared by clotting fibrinogen with the snake venom enzyme Batroxobin. (B)N-DSK differs from N-DSK in that it lacks FPA and, therefore, its molecular formula is (Aα 17-51, Bβ 1-118, γ 1-78)$_2$ with mol. wt. 55,000 (mol. wt. determined by gel electrophoresis)
(T)N-DSK : CNBr fragment obtained from human fibrin which had been prepared by clotting fibrinogen with human thrombin or by activating N-DSK with the same enzyme. (T)N-DSK lacks both FPA and FPB an has molecular formula (Aα 17-51, Bβ 15-118, γ 1-78)$_2$ with mol. wt. 52,000 (mol. wt. determined by gel electrophoresis)
CNBr : cyanogen bromide
SDS : sodium dodecyl sulfate
TPBS : phospate-saline buffer additionally containing 0.05% Tween 20
ELISA: Enzyme linked immunosorbent assay
RIA: Radioimmunoassay
A$_{490}$: Absorbance at a wavelength of 490 nm
Sac-Cel: donkey anti mouse cellulose suspension
Animal : unless indicated otherwise, "animal" used herein means any warm blooded animal other than human

SUMMARY OF THE INVENTION

There has now been discovered methods of preparing monoclonal antibodies. Such monoclonal antibodies are also monospecific. The novel monoclonal antibodies so produced are designated as MAb/1-8C6 and MAb/T2G1s. The hybridomas which express these monoclonal antibodies are designated as 1-8C6 (ATCC HB 8418) and T2G1s (ATCC HB 8426), respectively.

The method of producing the hybridomas and thus, the monoclonal antibodies, includes fusing an animal cell for example, a mouse myeloma cell, for example, mouse P3×63Ag8.653, with a spleen cell from an animal, for example, a mouse, for example, a BALB/cJ mouse.

In the case of MAb/1-8C6, a mouse is immunized with an $NH_2$-terminal fragment of human fibrinogen or fibrin I to form a novel hybridoma, i.e., 1-8C6. In the case of MAb/T2G1s, a mouse is immunized with the $NH_2$-terminal fragment of human fibrin II to form a novel hybridoma, i.e., T2G1s. The resultant hybridomas are separated and the hybridomas which produce the monospecific antibody to an $NH_2$-terminal fragment of human fibrinogen or fibrin I, in the case of MAb/1-8C6, and to an $NH_2$-terminal fragment of human fibrin II, in the case of MAb/T2G1s, are selected.

The fragment of human fibrinogen or fibrin I can be formed by cleavage of such human fibrinogen or fibrin I by CNBr. A fragment of human fibrinogen of such CNBr cleavage is N-DSK. Other fragments of human fibrinogen or fibrin I which can also be employed are $B\beta$ 1-118 and BB 1-42. A fragment of fibrin I which may be employed in the present invention is (B)N-DSK.

The fragment of human fibrin II, can be formed by cleavage of fibrin II by CNBr. A fragment of human fibrin II is (T)N-DSK. Other fragments of human fibrin II which can also be employed are $B\beta$ 15-118 and $B\beta$ 15-42.

Hybridoma cell line ATCC HB 8418, expresses a monospecific antibody, MAb/1-8C6, which reacts with the peptide fragment of the $B\beta$ chain of human fibrinogen or fibrin I containing amino acid residues 1-42, but does not react with peptide fragments of the $B\beta$ chain of human fibrinogen or fibrin I containing amino acid residues 1-14 or 15-42. As such, MAb/1-8C6 recognizes an epitope (antigenic determinant) in or around the $B\beta$ 14 Arg-15 Gly bond and thus distinguishes between $NH_2$-terminal peptides derived from the $B\beta$ chain of human fibrinogen, or fibrin I and fibrin II.

Hybridoma cell line ATCC HB 8426, expresses a monospecific antibody, MAb/T2G1s, which reacts with the peptide fragment of the $B\beta$ chain of human fibrin II containing amino acid residues 15-42, but does not react with peptide fragments of human fibrinogen or fibrin I containing amino acid residues 1-42 or 1-14. As such, MAb/T2G1s recognizes an epitope on the $B\beta$ chain of fibrin II, but not fibrinogen or fibrin I.

MAb/1-8C6 is monospecific for a single determinant on the $B\beta$ chain of human fibrinogen, fibrin I or peptides derived from either, which contain amino acid residues 1-42. MAb/1-8C6 contains no other anti-human fibrinogen antibodies. This is in contrast to prior art antisera which are inherently contaminated and to prior art monoclonal antibodies which are not specific for an epitope in or around the $B\beta$ 14 Arg-15 Gly bond.

MAb/T2G1s is monospecific for a single determinant on the peptide fragment of the $B\beta$ chain of human fibrin II containing amino acid residues 15-42. MAb/T2G1s contains essentially no other anti-human immune globulin, in contrast to prior art antisera which are inherently contaminated and in contrast to prior art monoclonal antibodies which are not specific for an epitope on the $B\beta$ chain of fibrin II.

MAb/T2G1s is also specific to human peptide fragments of fibrin II containing amino acid residues 15-42, i.e., MAb/T2G1s reacts with the products produced by thrombin digestion of human fibrinogen but does not react with the products resulting from thrombin digestion of certain animal fibrinogens, e.g., rabbit fibrinogen.

The novel hybridomas of the present invention can be cultured to produce antibody without the necessity of immunizing and killing animals, followed by the tedious adsorption steps necessary to obtain even the impure antisera of the prior art.

All immunoglobulin molecules consist of 2 identical light chains (MW 25,000) and 2 identical heavy chains (MW 50,000) held together as a tetramer by disulfide bonds. Each chain can be divided conceptually into specific domains or regions that have structural and functional significance. The half of the light chain toward the carboxy terminus is referred to as the constant region, while the amino-terminal half is the variable region of the light chain. Approximately one-quarter of the heavy chain at the amino terminus is referred to as its variable region, and the other three-quarters of the heavy chain are referred to as the constant regions of that heavy chain.

Four classes of heavy chains have been found in mice, and these classes can be distinguished by chemical differences. The type of heavy chain determines the class of immunoglobulin and thus its effector function. There are 5 immunoglobulin classes: IgG, IgA, IgM, IgD, and IgE. The four classes of mouse IgG are referred to as $IgG_1$, $IgG_{2a}$, $IgG_{2b}$ and $IgG_3$.

MAb/1-8C6 is of the class IgG and the subclass $IgG_{2a}$. MAb/T2G1s is of the class IgG and the subclass $IgG_1$.

Accordingly, the satisfaction of the foregoing advantages, this invention provides two hybridomas: one which produces antibodies to the peptide fragment of the $B\beta$ chain of human fibrinogen or fibrin I containing amino acid residues 1-42 and one which produces antibodies to the peptide fragment of the $B\beta$ chain of human fibrin II containing amino acid residues 15-42. This invention provides methods for preparing these hybridomas.

Still further, this invention provides a method for determination of the nature of the fibrinogen proteolysis pathway in vivo.

The present invention also provides methods for diagnosis of disease by employing the monoclonal antibodies of this invention.

The present invention also provides a method for the therapeutic removal of fibrin II from the bloodstream of a patient who is in danger of forming, or who is forming, occlusive thrombi.

In general, the hybridomas which express the monoclonal antibodies, according to the present invention, are prepared in accordance with the method of Köhler and Milstein. Following immunization of mice with a solution of N-DSK in the case of production of MAb/1-8C6 or (T)N-DSK in the case of production of MAb/T2G1s, the spleen cells of the immunized mice are fused with cells from a mouse myeloma line. The clone culture fluids from the resultant hybridomas are screened for those with supernatants containing antibody which give selective binding to the peptide fragment of the $B\beta$ chain of human fibrinogen or fibrin I containing amino acid residues 1-42 (in the case of production of MAb/1-8C6) or to the peptide fragment of the Bβ chain of human fibrin II containing amino acid residues 15-42 (in the case of production of MAb/T2G1s).

It should be emphasized that the unpredictable nature of hybrid cell preparation does not allow one to extrapolate from one antigen or cell system to another.

The monoclonal antibodies derived from the hybridomas produced by the methods of the invention are useful as diagnostic reagents in clinical studies to determine the nature of the fibrin molecule generated in the blood of any patient where thrombosis is imminent or manifest. Thrombosis is associated with a number of disease states but may also occur before, during or after surgery, as well as in other trauma states. The efficacy of heparin therapy for hemodialysis patients can also be checked by measuring the plasma concentration of fibrinogen or fibrin split products via the diagnostic reagent of the invention. The efficacy of thrombolytic therapy, using either streptokinase or tissue type plasminogen activator, may also be checked using the antibodies of the invention.

BRIEF DESCRIPTION OF DRAWINGS

FIG. 4 is a graph depicting inhibition of binding of $^{125}I$-Bβ 1-118 ligand by various "cold" competitors. A 1/40 dilution of MAb/1-8C6 was used and this bound about 40% of the ligand in absence of any competitor. Non-specific binding was less than 5%. Mean values of at least five different experiments are shown. No inhibition was observed with the other two chains of N-DSK (i.e. Aα 1-51 and γ 1-78) in the concentration range shown here. Fibrinogen, N-DSK and (B)N-DSK are dimers with 2 mol of Bβ chain (for fibrinogen) or Bβ 1-118 (both N-DSK species). Therefore, the operational mol. wt. used in the calculations was one-half the actual mol. wt. of each. The insert graph shows response data for fibrinogen and Bβ 1-118 which has been linearized by logit transforms.

FIG. 9 are graphs depicting HPLC elution patterns of the Bβ 1-42 peptide before (a) and after (b) digestion with human thrombin. The immunoreactivity profiles (shaded areas) of the fractions were obtained by a radioimmunoassay using $^{125}I$ Bβ15-42 ligand and rabbit antiserum to Bβ15-42 (Kudryk et al., supra, 1982). The amount of thrombin-digested peptide applied to the column in (b) was about 3×that in (a). Studies have shown that better than 70% of the antigen can be recovered in the indicated fractions.

DETAILED DESCRIPTION OF THE INVENTION

Figure 1:
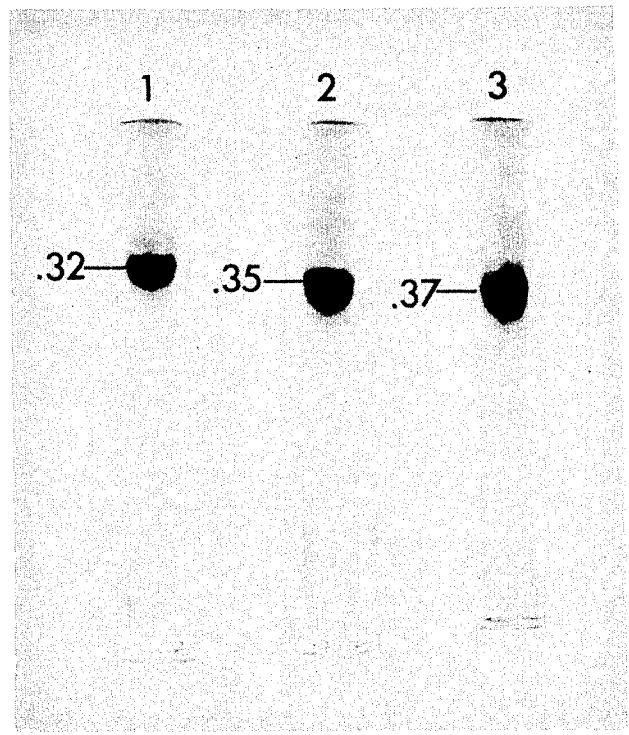
FIG. 1 depicts electrophoretic patterns of N-DSK(1), (B)N-DSK(2), and (T)N-DSK (3) on 7% polyacrylamide gels in SDS. The mobility of each N-DSK species is indicated. (B)N-DSK was isolated from Batroxobin-induced fibrin and (T)N-DSK was prepared from N-DSK by digestion with human thrombin.

The methods of preparing hybridomas and the antibodies expressed by such hybridomas, according to the present invention, can be conducted by fusing a transformed animal cell such as a myeloma cell with an animal spleen cell. It is preferred, however, to use mouse myeloma cells and mouse spleen cells and therefore, the present invention is hereinafter described using mouse myeloma cells and mouse spleen cells.

The method of preparing the hybridomas which express either MAb/1-8C6 (which reacts with a peptide fragment of the Bβ chain of human fibrinogen or fibrin I containing amino acid residues 1-42 but which does not react with a peptide fragment of the Bβ chain of human fibrinogen or fibrin I containing amino acid residues 1-42 or 15-42) or MAb/T2G1s (which reacts with a peptide fragment of the Bβ chain of human fibrin II containing amino acid residues 15-42 but which does not react with a peptide fragment of the Bβ chain of human fibrinogen or fibrin I containing amino acid residues 1-14 or 1-42), according to the present invention, generally comprises the following steps:

A. Immunizing mice with either N-DSK, Bβ 1-118, Bβ 1-42 or (B)N-DSK, for production of MAb/1-8C6, or (T)N-DSK, Bβ 15-118 or Bβ 15-42, for production of MAb/T2G1s. N-DSK is prepared from fibrinogen and (T)N-DSK is prepared by thrombin digestion of N-DSK. While BALB/cJ mice are preferred, other mouse strains can be used. The immunization schedule and immunogen concentration should be such as to produce useful quantities of suitably primed splenocytes. To produce MAb/1-8C6, mice are immunized intraperitoneally (i.p.) with 0.1 ml of an emulsion of N-DSK solution (4 mg/ml) and an equal volume of complete Freund's adjuvant followed by four booster injections of the same dose using incomplete Freund's adjuvant at weekly intervals, followed by an intravenous (i.v.) boost using O.1mg N-DSK in Tris-saline 10 weeks later. To produce MAb/T2G1s, mice are immunized i.p. with 100 μg (T)N-DSK mixed with complete Freund's adjuvant, followed by four booster i.v. injections of the same dose using incomplete Freund's adjuvant, followed by an i.v. boost with 100 μg (T)N-DSK in Tris-saline.

B. Removing the spleen from each immunized mouse and making a suspension of the cells from each spleen in an appropriate medium, e.g., RPMI 1640.

C. Fusing the suspended spleen cells with mouse myeloma cells from a suitable cell line, e.g., by the use of suitable fusion promoter, e.g., PEG 1000. The preferred ratio is about four spleen cells per myeloma cell in the case of MAb/1-8C6 production and seven spleen cells per myeloma cell in the case of MAb/T2G1s. A total volume of about 0.5-1.0 ml of fusion medium is appropriate for about $10^8$ splenocytes. Many mouse myeloma cell lines are known and available, generally from members of the academic community or various deposit banks, such as the Salk Institute Cell Distribution Center, La Jolla, CA. The cell line used preferably is of the so-called "drug resistant" type, so that unfused myeloma cells do not survive in a selective medium, while hybrids survive. The most common class is 8-azaguanine resistant cell lines, which lack the enzyme hypoxanthine guanine phophoribosyl transferase and hence are not supported by HAT (hypoxanthine, aminopterin, and thymidine) medium. It is also generally preferred that the myeloma cell line used be of the so-called "non-secreting" type, in that it does not itself produce any antibody, although secreting types may be used. In certain cases, however, secreting myeloma lines may be preferred.

While the preferred fusion promoter is polyethylene glycol having an average molecular weight from about 1000 to about 4000 (commercially available as PEG 1000, etc.), other fusion promoters known in the art may be employed.

D. Diluting and culturing in separate containers, e.g., separate wells of a microtiter plate, the mixture of unfused spleen cells, unfused myeloma cells, and fused cells in a selective medium which do not support the unfused myeloma cells for a time sufficient to allow death of the unfused cells (about 14–16 days). The dilution may be a type of limiting one, in which the volume of diluent is statistically calculated to isolate a certain number of cells (e.g. 1–4) in each separate container (e.g., each well of a microtiter plate). The medium is one (e.g., HAT medium) which will not support the drug resistant (e.g., 8-azaguanine resistant) unfused myeloma cell line. Hence, these myeloma cells perish. Since the unfused spleen cells are non-malignant, they have only a finite number of generations. Thus, after a certain period of time (about 14–16 days) these unfused spleen cells fail to reproduce. The fused cells, on the other hand, continue to reproduce because they possess the malignant quality of the myeloma parent and the ability to survive in the selective medium.

E. Evaluating the supernatant in each container (well) containing a hybridoma for the presence of antibodies to (1) N-DSK and related structures [fibrinogen, N-DSK, or their fragments, for example, (B)N-DSK (Batroxobin digest of N-DSK) and Bβ 1-118] and not to the Aα 1-51 or γ 1-78 chains of N-DSK, thrombin digested Bβ 1-118, (T)N-DSK, free Bβ 1-14 (FPB) or Bβ 15-42, in the case of production of MAb/1-8C6, and (2) to (T)N-DSK and related structures (fibrin II, (T)N-DSK, thrombin-digested Bβ 1-42 and Bβ 15-42) and not to intact fibrinogen, N-DSK or (B)N-DSK or Bβ1-42 in the case of production of MAb/T2G1s.

F. Selecting (e.g., by limiting dilution) and cloning a hybridoma or hybridomas producing the desired antibody, e.g. antibody which reacts with a peptide fragment of the Bβ chain of human fibrinogen or fibrin I containing amino acid residues 1-42, but does not react with either of the peptide fragments of said Bβ chain containing only amino acid residues 1-14 or 15-42, in the case of MAb/1-8C6, or antibody which reacts with a peptide fragment of the Bβ chain of human fibrin II containing amino acid residues 15-42, but does not react with a peptide fragment of the Bβ chain of human fibrinogen or fibrin I containing amino acid residues 1-14 or 1-42, in the case of MAb/T2G1s.

Once the desired hybridoma has been selected and cloned, the resultant antibody may be produced in one of two ways. The purest monoclonal antibody is produced by in vitro culturing of the desired hybridoma in a suitable medium for a suitable length of time, followed by recovery of the desired antibody from the supernatant of the clones. The suitable medium and suitable length of culturing time are known or are readily determined. This in vitro technique produces monoclonal antibody, free from other antihuman immune globulin. There is a small amount of other immune globulin present since the medium contains xenogeneic serum (e.g., fetal calf serum). However, this in vitro method may not produce a sufficient quantity or concentration of antibody for some purposes, since the concentration of monoclonal antibody is only about 50 μg/ml.

To produce a much greater concentration of slightly less pure monoclonal antibody, the desired hybridoma clones may be transferred, i.e., intraperitoneally injected into mice, preferably syngenic or semi-syngenic mice. The hybridoma forms antibody-producing tumors after a suitable incubation time, which results in a high concentration of the desired antibody (about 5–20 mg/ml) in the bloodstream and peritoneal exudate(ascites) of the host mouse. Although these host mice also have normal antibodies in their blood and ascites, the concentration of these normal antibodies is only about 5% of the monoclonal antibody concentration. Moreover, since these normal antibodies are not antihuman in their specificity, the monoclonal antibody obtained from the harvested malignant ascites or from the serum is essentially free of any contaminating antihuman immune globulin. This monoclonal antibody is high titer and high ratio of specific to non-specific immune globulin.

A process by means of which a technician can test a plasma sample to determine the amount of antigens (e.g., the amount of a peptide fragment of the Bβ chain of human fibrinogen of fibrin I containing amino acid residues, 1-42, in the case of MAb/1-8C6, or the amount of a peptide fragment of the BB chain of human fibrin II containing amino acid residues 15-42, in the case of MAb/T2G1s) present for which the monoclonal antibodies of the invention are monospecific, is as follows:

Blood is collected from a patient at selected intervals and the plasma derived therefrom. The plasma sample is quickly "processed", i.e., treated with ice-chilled ethanol [50% final concentration] in order to isolate fibrinogen/fibrin peptides derived from the Bβ chain. The ethanol supernatant is generally freeze dried so as to concentrate the extract as well as to remove the solvent. The "processed" plasma sample can be split into two fractions, one which is used to detect the presence of Bβ 1-42 and one which is used to detect the presence of Bβ 15-42. The level of peptides present in the ethanol extract can be determined by either radioimmunoassay (RIA) or enzyme-linked immunosorbent assay (ELISA). For example, different dilutions of the ethanol extract are mixed with fixed amounts of animal monoclonal antibody, for example, MAb/1-8C6, and the competitive radio-labeled antigen consisting of, for example, a radioactively labeled peptide fragment of the Bβ chain of human fibrinogen or fibrin I containing amino acid residues 1-42, e.g. $^{125}$I Bβ 1-42 ligand which competitive radio-labeled antigen can bind with the animal monoclonal antibody, e.g., MAb/1-8C6. Different dilutions of the ethanol extract are also mixed with fixed amounts of animal monoclonal antibody, for example, MAb/T2G1s and the competitive radio-labeled antigen consisting of a radioactively labeled peptide fragment of the Bβ chain of human fibrin II containing amino acid residues 15-42, which competitive radio-labeled antigen e.g., $^{125}$I Bβ15-42 ligand can bind with the animal monoclonal antibody, e.g. MAb/T2G1s. In both cases, after a suitable incubation period, a second antibody specific to animal monoclonal antibody, e.g., MAb/1-8C6 or MAb/T2G1s, as the case may be, (e.g., rabbit anti mouse whole antibody or Sac-Cel) is added. Following a second incubation period, antibody bound radio-labeled antigen (ligand) is separated and quantitated, i.e., the radioactivity of the bound radio-labeled antigen is counted. The more "cold" Bβ 1-42 (or 15-42) peptide is present in a sample, the less bound ligand will be observed for that sample. The precise amount (i.e., the concentration of the Bβ 1-42 or 15-42 peptide) in the unknown sample may be determined by comparing the inhibition value of the unknown with that obtained using a Bβ 1-42 or 15-42 standard, respectively, i.e., comparing the results of the RIA test using the plasma sample with that obtained using a standard amount of known antigen, e.g., a peptide fragment of the Bβ chain of human fibrinogen or fibrin I containing amino acid residues 1-42 or a peptide fragment of the Bβ chain of fibrin II containing amino acid residues 15-42.

Alternatively, the presence of the same antigens (i.e., Bβ 1-42 and 15-42) can be detected by ELISA. In this method, a solid support, e.g., microtiter plates, are coated overnight with competitive antigen consisting of, for example, a peptide fragment of the Bβ chain of human fibrinogen or fibrin I containing, e.g., either Bβ 1-42, N-DSK or intact fibrinogen. After a wash and "block" (minimizes non-specific binding) procedure, an appropriate dilution of MAb/1-8C6 and unknown peptide antigen in a plasma sample (or Bβ 1-42 standard) is added to the appropriate wells of the microtiter plate. If there is a large excess of Bβ 1-42 peptide in such a sample, MAb/1-8C6 will react with the peptide and little, if any, of this antibody will be available for binding to the same or related antigen which was initially coated on the surface of the microtiter plate (see above). The amount of antibody, for example, MAb/1-8C6, if any, bound to the antigen coated plate, is detected by determining the amount of enzyme-linked antibody bound to the plate, which antibody binds to, i.e., is specific to mouse immunoglobulin, for example, to MAb/1-8C6, by methods already described (Engvall, E., In *Methods in Enzymology*, 70, Part A, 419–439, 1980). The amount of, for example, BB 1-42, in the unknown sample is determined by comparing the inhibition value of the unknown with that obtained using, for example, a Bβ 1-42 standard (i.e., comparing the results of the ELISA test using the plasma sample with that obtained using a standard amount of known antigen, i.e., a peptide fragment of the Bβ chain of human fibrinogen or fibrin I containing amino acid residues 1-42. The same ELISA procedure is used to detect the presence of Bβ15-42 in a plasma sample. For example, the microtiter plates are coated with competitive antigen consisting of a peptide fragment of the Bβ chain of human fibrin II containing amino acid residues 15-42, e.g. Bβ 15-42. MAb/T2G1s and the unknown peptide antigen in a plasma sample (or Bβ 15-42 standard) are added to the wells of the plate. The amount of MAb/T2G1s bound to the antigen coated plate is detected by determining the amount of enzyme-linked antibody bound to the plate, which antibody binds to, i.e., is specific to mouse immunoglobulin, for example, to MAb/T2G1s. The amount of Bβ 15-42 in the unknown sample is determined by comparing the inhibition value of the unknown with that obtained using a Bβ 15-42 standard (i.e., comparing the results of the ELISA test using the plasma sample with that obtained using a standard peptide fragment of the Bβ chain of human fibrin II containing amino acid residues 15-42.

A process by which a technician can detect the potential for the onset of occlusive thrombosis in a patient entails dividing the plasma sample into two fractions and determining (1) the amount of a peptide fragment of the Bβ chain of human fibrinogen or fibrin I containing amino acid residues 1-42 in one fraction, and (2) the amount of the Bβ chain of human fibrin II containing amino acid residues 15-42 in the other fraction. The technician can use either the ELISA or RIA tests as described above. The relative amounts of the peptide fragments in the plasma of a patient can then be compared. If Bβ 1-42 predominates over Bβ 15-42, this indicates that plasmin proteolysis of fibrinogen or fibrin I polymer is taking place. If Bβ 15-42 predominates over Bβ 1-42, this indicates that fibrin II has been formed, i.e., the potential for the onset of occlusive thrombosis in the patient.

The present invention also concerns test kits for determining the nature of in vivo generated peptides of fibrinogen and/or fibrin. One such test kit, i.e., a single peptide detection kit, for example, detects the presence of the peptide fragment of the Bβ chain of human fibrinogen or fibrin I containing amino acid residues 1-42. An aliquot (e.g., 0.5 mg) of lyophilized animal monoclonal antibody for example, MAb/1-8C6, is provided. An aliquot, (e.g., 2-4 mg) of fibrinogen is also provided, which the technician uses to coat the microtiter plate to be used in ELISA testing. An aliquot (e.g., 20 µg) of the peptide fragment of the Bβ chain of human fibrinogen or fibrin I containing amino acid residues 1-42 is further provided. This is to be used by the technician to prepare a standard curve wherein the amount of MAb/1-8C6 which binds to the fibrinogen-coated ELISA plate, as shown by color intensity (as explained below), decreases as the amount of competing antigen (Bβ 1-42) in the test sample solution increases. The technician prepares dilutions of the Bβ 1-42 provided, to obtain known amounts of antigen to be used in solution in competitive ELISA testing, which technique is well known. An enzyme-linked (e.g., peroxidase-conjugated) immunoglobulin (e.g., rabbit) to animal, for example, mouse immunoglobulin is also provided to detect binding of the animal immunoglobulin, for example, MAb/1-8C6, to the fibrinogen-coated plate. Enzyme-linked IgG binding is detected using a $H_2O_2$ and o-dianisidine solution. Color intensity can be measured automatically using, for example, an MR 580 Microelisa Autoreader (Dynatech, Alexandria, VA).

Once the standard curve is prepared, the ELISA test can be performed using the plasma sample which is processed to remove fibrinogen (for example, as described below in Example 7) which plasma sample may contain an unknown amount of Bβ 1-42. The color intensity is measured and the amount of Bβ 1-42 in the plasma sample can be "read" from the standard curve.

Another test kit, i.e., a single peptide detection kit, in accordance with the present invention, operates as explained above, but measures the amount of Bβ 15-42 present in a plasma sample. An aliquot of lyophilized animal monoclonal antibody, for example, MAb/T2G1s (e.g., 0.5 mg), is provided which is used to coat the microtitre plate. An aliquot (e.g., 20 µg) of the peptide fragment of the Bβ chain in human fibrin II containing amino acid residues is also provided, as is an enzyme-linked immunoglobulin, (e.g., rabbit) to animal, e.g., mouse immunoglobulin.

A third test kit, i.e., a peptide detection kit for detection of two different peptides, in accordance with the present invention, and which is the preferred test kit of the invention, can be used to determine both Bβ 1-42 and Bβ 15-42 in a plasma sample. The plasma sample is split into two fractions, one which is used to test for the presence of Bβ 1-42 and one which is used to test for the presence of Bβ 15-42. Animal monoclonal antibodies, for example, MAb/1-8C6, MAb/T2G1s, fibrinogen and fibrin (to coat the plates), Bβ 1-42 and Bβ 15-42 (to prepare standard curves) and enzyme-linked immunoglobulins, e.g., rabbit, to the animal, e.g., mouse immunoglobulin are all provided. The technician follows the procedures described above for each single peptide detection kit. In this way, the amounts of Bβ 1-42 and Bβ 15-42 can be measured and compared in each plasma sample.

The use of ELISA, as described above, is preferred. The technician can, however, use the components of the kit to perform RIA, instead, to determine the amounts of the peptide fragments.

As described above, the invention provides a means for quick analysis of the nature of the fibrin molecule being produced in vivo. If the Bβ 1-42 antigen is predominant over the Bβ 15-42 antigen in the plasma test specimen, this is an indication that plasmin proteolysis of fibrinogen or fibrin I polymer is taking place. On the other hand, if the Bβ 15-42 antigen is predominant over the Bβ 1-42 antigen, this is a signal to the clinician that fibrin II is in the circulation or may be depositing on the vessel walls, a process which may lead to occlusive thrombosis.

Although it is preferred to use spleen cells from immunized mice and mice myeloma cells for the present invention, it is also contemplated that cells from other animals, for example, rats, guinea pigs and rabbits can be used.

The procedures of the present invention can also be employed to generate antibodies to fibrinogen or fibrin I fragments from species other than human. Fragments from rabbit or dog fibrinogen, fibrin I or fibrin II can be used, for example, to generate antibodies to fibrinogen or fibrin I fragments for veterinary uses. Such antibodies can also be used in studies dealing with experimental thrombosis or thrombolytic therapy. It should be noted, however, that when treating a particular species of animal, the antibody should be derived from a different species of animal.

The assay of the present invention can be used to measure fibrinogen or fibrin degradation products in a number of trauma patient groups, for example, burn patients, patients suffering head and other bodily injuries, patients undergoing surgery (assays can be done before, during and after surgery), including open-heart and coronary bypass surgery, hemodialysis patients, cancer patients and patients with deep-vein thrombosis. Elderly patients undergoing hip surgery, for example, may develop acute deep-vein thrombosis. To alleviate this condition, two therapeutic procedures may be employed, i.e., surgery to remove thrombin (clots) or dissolution of thrombin by fibrinolytic agents such as streptokinase or tissue-type plasminogen activator (t-PA). The procedures of the present invention can be used to detect the earliest stages of clot dissolution as indicated by the aforementioned thrombolytic agents. The procedures of the present invention can be used for detection of fibrinogen or fibrin degradation products in any patients who may or potentially may suffer from occlusive thrombosis.

The MAb/T2G1s of the present invention can be used therapeutically, to remove fibrin II from the bloodstream of a patient who may be developing occlusive thrombi. For example, hemodialysis can be used to effect such removal. Using hemodialysis, the MAb/T2G1s is immobilized on a solid support, e.g., glass beads. The immobilized MAb/T2G1s-solid support complex is then placed within the hemo dialysis chamber at a location in the chamber before the blood is returned to the patient. Accordingly, during hemodialysis, the passing of the blood through the hemodialysis chamber such that the blood contacts the immobilized monoclonal antibody, essentially "cleanses" the blood of fibrin II before the blood is returned to the circulatory system of the patient.

The present invention is further described hereinbelow by reference to the following non-limiting examples.

EXAMPLES

Example 1

Preparation of N-DSK, (T)N-DSK & related fragments

Human fibrinogen was obtained from IMCO Corporation Ltd. (Stockholm, Sweden). N-DSK was prepared from the fibrinogen essentially following the technique of Blomback et al., J. Biol. Chem., 248, 5804–5820, 1973. Instead of using counter-current distribution, however, ion-exchange chromatography on Sephadex DEAE A50 (Pharmacia, Piscataway, New Jersey) was employed.

Partially pure N-DSK was applied to the ion-exchange resin in 0.1M Tris, pH 7.5. The N-DSK was eluted from the column with a linear salt gradient made with 0.1M Tris, pH 7.5 (start buffer) and 0.1M Tris, pH 7.5, additionally containing 0.3M NaCl (limit buffer). N-DSK or N-DSK - containing fractions from any stage of the purification procedure were never concentrated by freeze-drying.

(T)N-DSK and (B)N-DSK were prepared from thrombin [human thrombin, 3000 NIH units/mg protein (Sigma, St. Louis, MO)] and Batroxobin [insolubilized enzyme from venom of *Bathrops atrox marajoensis*, 20 Batroxobin units /ml suspension (Pentapharm Ltd., Basle, Switzerland)] digestion of fibrin gels, respectively. Fibrinogen solutions were made as described by Koehn and Canfield, *Analyt. Biochem.*, 116, 349–356, 1981. Clotting was initiated by adding 5 units /ml (thrombin or Batroxobin) and digestion was continued for about 6 hours at 37° C. Cleavage with CNBr and all subsequent isolation procedures were identical to that described above for N-DSK. (T)N-DSK was also prepared directly from N-DSK. Solutions (0.5–1.0 mg/ml) of the latter were made of 0.1 M Tris containing 0.15M NaCl, pH 7.5 and these were later split in two equal fractions. Thrombin (10 NIH units/ml) was added to one aliquot and an equal volume of saline added to the other. Both samples were incubated at 37° C. for 4 hours, after which time, an aliquot (10μl of a $0.9 \times 10^{-4}$ M stock solution /ml digest) of the highly specific thrombin inhibitor D - Phe - Pro - Arg - $CH_2Cl$ (Calbiochem - Behring, San Diego, California) was added to both samples. Fibrinopeptide A (FPA) and Fibrinopeptide B (FPB) radioimmunoassays were used to measure the thrombin cleavage products. The FPA assay was made using the kit and procedure supplied by IMCO Corporation Ltd. (Stockholm, Sweden). The FPB assay was made in accordance with the procedure of Bilezikian et al., *J. Clin. Invest*, 56, 438–445, 1975. Chains of N-DSK as well as plasmin degradation products of fibrinogen were prepared as previously described (Blombäck et al., J. Biol. Chem., 241 1496–1512, 1972 and *J. biol. Chem.*, 248, 5806–5820, 1973; Gardlund et al., Thromb. Res., 1, 371–388, 1972).

Various techniques were employed to determine the purity of N-DSK and its related fragments. Analytical and preparative chromatography were performed using the 1084B Hewlett-Packard liquid chromatography. The column and chromatography conditions were as described by Koehn and Canfield, *Analyt. Biochem.*, 116, 349–356 1981. Electroimmunoassay for N-DSK and related structures was similar to that described previously (Kudryk et al., supra 1982). Gels were made by mixing N-DSK antisera (2416) with hot gel solutions to give an antisera concentration of about 0.4%. Gel electrophoresis and amino acid analysis were as described (Blombäck et al., J. Biol. Chem, 248, 5806–5820, 1973; Hessel et al., Eur. J. Biochem., 98, 521–534, 1979).

Figure 2A:
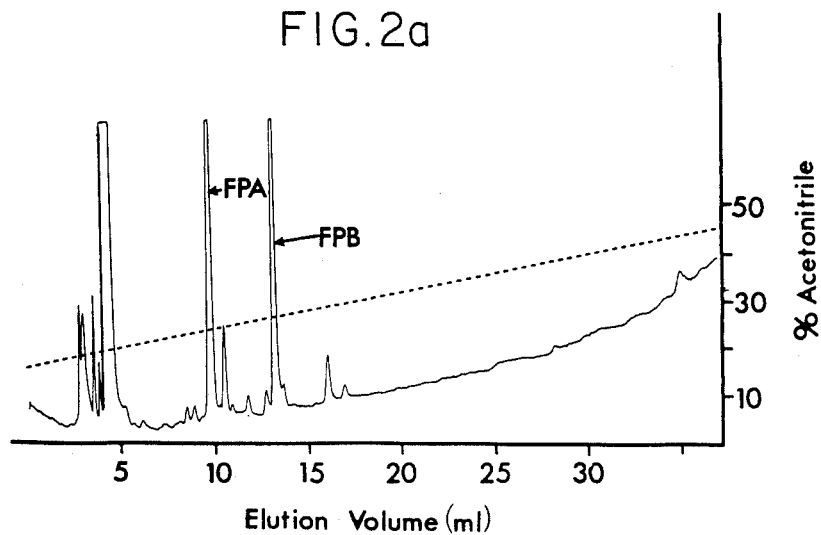
FIG. 2a and FIG. 2b are graphs depicting fractionation of thrombin-cleaved peptides from N-DSK (FIG. 2a) and (B)N-DSK (FIG. 2b) by high-performance liquid chromatography. The elution patterns were obtained by meauring absrbance at 206nm. The column and chromatography conditions were similar to those described by Koehn and Canfield, *Analyt. Biochem.*, 116, 349–356, 1981.
Figure 2B:
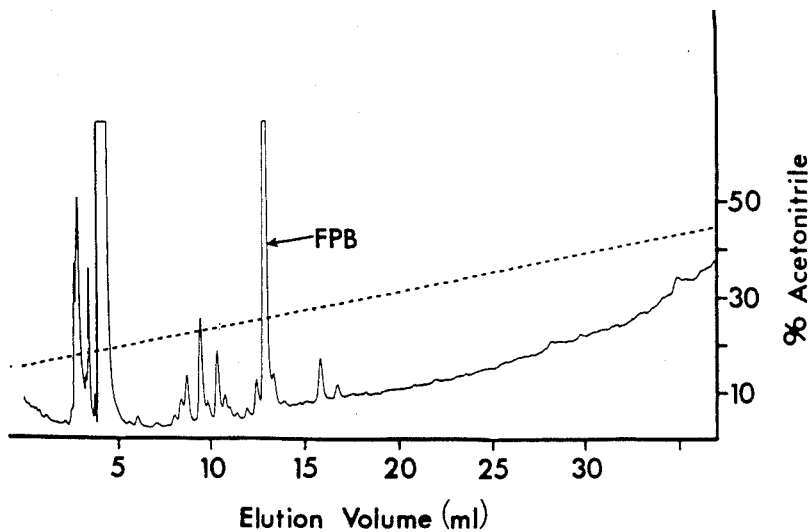

The disulfide-bonded N-DSK, (T)N-DSK and (B)N-DSK showed slight but detectable differences in mobility on 7% acrylamide gels in SDS as illustrated in FIG. 1. Following reduction, a characteristic band pattern for chains of each fragment was obtained on 10% acrylamide gels in SDS (not shown). That is, N-DSK and (B)N-DSK differed only in the mobility of the Aα chain. By comparison with N-DSK, reduced (T)N-DSK showed different mobility for both the Aα and Bβ chains. These observations were consistent with those reported by others (Hessel, Doctoral thesis, Chem. Dept. Karolinska Institutet, Stockholm, Sweden, 1975; Hessel et al., *Eur. J. Biochem.*, 98, 521–534, 1979). In order to determine the the component fibrinopeptide content of each, the three N-DSK species were treated with thrombin. Following this, each digest was adjusted to 9% trichloracetic acid and the thrombin-cleaved peptides, if any, were isolated from the supernatant using adsorption on Sep-Pak $C_{18}$ cartridges as previously described (Koehn and Canfield, supra, 1981). The peptides were later identified by high-performance liquid chromatography (HPLC) as shown in FIG. 2. Both FPA and FPB were released from N-DSK (FIG. 2a). The major peptide recovered from a thrombin digest of (B)N-DSK was FPB (FIG. 2b). No peptides were released from gel filtered (T)N-DSK when it was digested with thrombin a second time.

The component chains of N-DSK exhibited single bands on 10% acrylamide gels and gave amino acid compositions which were consistent with those already described (Blombäck et al., supra, 1972, 1973; Hessel et al., supra, 1979).

The peptide Bβ1-42 was prepared by activating plasminogen-containing fibrinogen solutions as follows. IMCO fibrinogen (Lot F-171) was diluted to a concentration of about 4.0 mg/ml in 0.05M Tris, pH 7.4. After adding 100 U/ml streptokinase [Lot 112F-0373), 4500 U/mg solid, Sigma, St. Louis, MO], digestion was allowed to proceed at 37° C./60 min. Following this time, most of the non-digested fibrinogen was precipitated by heating at 60° C./30 min. After centrifugation, the supernatant was passed on a Sep-Pac $C_{18}$ cartridge (Waters Associates, Milford, MA). The adsorbed peptides, including Bβ1-42, were eluted using 50% acetonitrile. High performance liquid chromatography (HPLC) was later used in an effort to purify the Bβ1-42 peptide. The column and procedure were essentially those described by Koehn & Canfield, Analyt. Biochem. 116, 349–356, 1981.

The peptides released from fibrinogen as consequence of streptokinase activation gave a very complex HPLC pattern (not shown). By following the immunoreactivity of the HPLC fractions with the Bβ15-42 radioimmunoassay as previously described (Kudryk et al., supra, 1982), several reactive peaks were obtained. One of these was isolated in preparative HPLC runs. As shown in of FIG. 9a, the peak eluting at or near fraction 16 reacted with rabbit antiserum to Bβ15-42. These results were expected since this antiserum does not distinguish Bβ15-42 from Bβ1-42 (Kudryk et al., supra, 1982). When an aliquot of this same material, Bβ1-42, was digested with human thrombin and re-chromatographed under the same conditions, the pattern shown in FIG. 9b was observed. As a consequence of thrombin digestion, the peak shown in FIG. 9a disappeared and two new peaks appeared. One of these eluted at or near fractions 6–8 and reacted in the B$\beta$15-42 immunoassay. This material was identified as B$\beta$15-42 and resulted from thrombin cleavage of B$\beta$1-42 at the 14 Arg-15 Gly bond. The IMCO standard B$\beta$15-42 also eluted in this position when separated by HPLC under the same conditions (not shown). The second peak, eluting at or near fraction 21, was identified as FPB. This was established from the known elution position of the FPB standard in the HPLC system. In addition, the fraction 21 peak reacted in the FPB radioimmunoassay (not shown).

The peptide B$\beta$15-42 was obtained from IMCO or prepared directly from B$\beta$1-42 by digestion, as described above, with human thrombin [3000 NIH units/mg protein, Sigma, St. Louis, MO]. In the latter procedure, B$\beta$1-42 was dissolved in 0.2M NH$_4$HCO$_3$ (pH 8.0) and digestion was at 37° C./90 min. After this time, an aliquot (10 $\mu$l of a $0.9 \times 10^{-4}$ M stock solution per ml digest) of the highly specific thrombin inhibitor D-Phe-Pro-Arg-CH$_2$Cl (Calbiochem-Behring, San Diego, CA) was added in order to stop digestion.

Example 2

Production of Monoclonal Antibodies

To produce MAb/1-8C6, BALB/cJ mice (Jackson Laboratories, Bar Harbor, ME.) were each immunized intraperitoneally (i.p.) with 0.1 ml of an emulsion of N-DSK solution (4 mg/ml) and an equal volume of complete Freund's adjuvant. To produce MAb/T2G1, BALB/cJ mice were each immunized i.p. with 100 $\mu$g (T)N-DSK mixed with complete Freund's adjuvant. In both cases, the mice were boosted 4 times with the same dose (using incomplete Freund's adjuvant) at weekly intervals. In the case of MAb/1-8C6 production, the animals were boosted intravenously (i.v.) after a 10-week pause, using 100 ug N-DSK in Tris-saline. In the case of MAb/T2G1 production, the animals were boosted five weeks after the initial injection, i.v., with 100 $\mu$g (T)N-DSK in Tris-saline. In both cases, spleens were removed from the mice three days later and a single cell suspension was made by pressing the tissue through a stainless steel mesh.

Cell fusion in both cases was performed according to the procedure developed by Kohler and Milstein, *Eur. J. Immun.*, 6, 511–519, 1976. Spleen cells were fused with myeloma cells [P3X63Ag8.653] at a ratio of either 4:1 (MAb/1-8C6) or 7:1(MAb/T2G1s) in 35% polyethylene glycol-1000 (Koch-Light Labs, Colmbrook, U.K.) in RPMI 1640 medium (GIBCO Labs, Grand Island, N.Y.) at room temperature for 1 minute. Cells were pelleted, washed and resuspended in 215 ml RPMI 1640 containing 10% (MA Bioproducts, Walkersville, MD) and 20% fetal calf serum (Sterile Systems, Logan, VT). Normal spleen cells (10$^8$) were added as a feeder layer. Following overnight incubation in a humidified 5% CO$_2$ atmosphere at 37° C., hypoxanthine-aminopetrin - thymidine (HAT) medium (Littlefield, Science, 145, 709–710, 1964) was added to start HAT selection. After overnight incubation at 37° C. in 5% CO$_2$, cells in the same HAT medium were cloned by limiting dilution in 96 - well culture plates [Costar 3596 (Cambridge, MA.)] Hybridoma clones were cultured for 16 days and then media were assayed for antibody.

Example 3

Detection of anti N-DSK and anti (T)N-DSK antibodies produced by hybridomas

Initial testing of hybridoma culture media was by the ELISA method of Engvall, Methods in Enzymology, 70 (Part A), 419–439, 1980, Acad. Press, N.Y. Clone culture fluids were screened on polyvinyl microtiter plates (Costar, Cambridge, MA.), each well containing one of six antigens: fibrinogen, N-DSK, (T)N-DSK, the A$\alpha$ 1-51, B$\beta$1-118 or $\gamma$ 1-78 chains of N-DSK, at a concentration of about 5-15 $\mu$g/ml in Na$_2$CO$_3$/NaHCo$_3$, pH 9.6. An aliquot of undiluted clone culture fluid was added to each of the six "antigen" wells. After an incubation and subsequent wash cycle, an appropriate dilution of peroxidase - conjugated rabbit immunoglobulin to mouse immunoglobulin [Accurate Chemicals, Westbury, N.Y.] reagent was added. Enzyme-linked IgG binding was detected using a H$_2$O$_2$ and o-dianisidine solution. Color intensity was measured automatically using the MR580 Microelisa Autoreader (Dynatech, Alexandria, VA.).

Of the 182 hybridoma clones tested for detectable anti - N-DSK antibodies, one (ATCC HB 8418) produced a very high concentration of antibody which reacted not only with the immunogen (N-DSK) but also with intact fibrinogen, (B)N-DSK, B$\beta$ 1-118 and B$\beta$ 1-42. A large quantity of MAb/1-8C6 was obtained by culturing the hybridoma in RPMI 1640 containing 10% NCTC 109 and 20% fetal calf serum.

Figure 3:
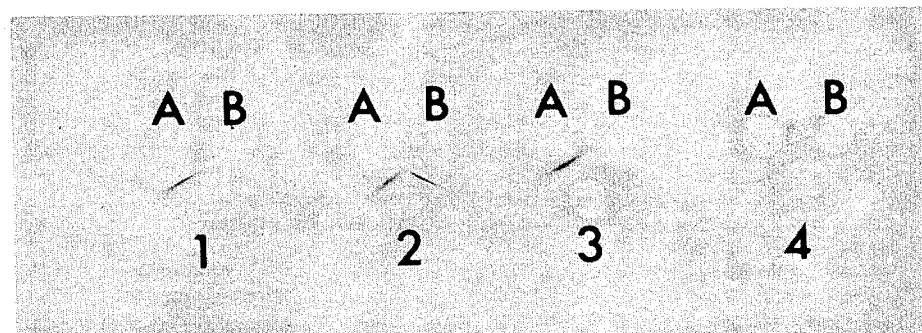
FIG. 3 depicts an Ouchterlony analysis of MAb/1-8C6 using class-specific antisera. The antigens were normal mouse plasma (A) and MAb/1-8C6(B); the class specific antisera were: anti $IgG_1$ (1); anti $IgG_{2a}$(2); anti $IgG_{2b}$(3); anti $IgG_3$(4).

Later, MAb/1-8C6 was purified by precipitation with half-saturated ammonium sulfate and the IgG obtained from the second precipitation was dissolved in 0.1 M Tris containing 0.02% NaN$_3$ (pH 7.5). The final solution was 1/10 the original volume of culture medium. Determination of IgG class was tested in Ouchterlony using rabbit anti-mouse immunoglobulin class-specific antisera (Litton Bionetics Inc., Charleston, SC). As shown in FIG. 3, MAb/1-8C6 reacted only with IgG$_{2a}$ antiserum. The light-chain class of the antibody was not determined.

Of the 1632 hybridoma clones tested for anti-(T)N-DSK antibodies, 247 clones produced a very high concentration of such antibodies. Most of these clone culture fluids also reacted with N-DSK and fibrinogen coated plates. However, clone T2G1 produced antibodies which, in addition to binding all the three coated plates mentioned above, also bound the $^{125}$I B$\beta$15-42 ligand in solution. Due to its varied cross-reactivity, T2G1 was deemed to be a mixed clone and, therefore, was subcloned. From the latter procedure, one single clone (T2G1s) out of the 96 tested was shown to secrete an antibody which, on ELISA, reacted only with (T)N-DSK coated plates and was also capable of binding $^{125}$I B$\beta$15-42 ligand in solution.

After subcloning, a mass culture of clone T2G1s was prepared in RPMI 1640 containing 10% NCTC 109 and 20% fetal calf serum. The antibody [MAb/T2G1s] which accumulated in the spent medium of this hybridoma was purified by precipitation with half-saturated ammonium sulfate and the IgG obtained from the second precipitation was dissolved in 0.1M Tris containing 0.02% NaN$_3$ (pH 7.5). The final solution was 1/10 the original volume of culture medium. As determined by Ouchterlony testing as described above, MAb/T2G1s reacted only with IgG$_1$ antiserum. The light chain class of MAb/T2G1s was not determined.

Example 4

Specificity of MAb/1-8C6 for N-DSK and related structures

As previously described, the original culture fluid from hybridoma clone 1-8C6 (ATCC HB8418) was tested by ELISA on plates coated with N-DSK or any of the related structures mentioned earlier. Strongly positive reactions were obtained on plates with either N-DSK, fibrinogen or Bβ 1-118. Plates coated with (T)N-DSK, Aα 1-51 or γ1-78 did not react. The specificity of MAb/1-8C6 was further checked by competitive immunoassay using both the ELISA and radioimmunoassay methods. The ELISA was a two-step procedure. Microtiter plates were coated with BB 1-118 (5 ug/ml) at +4° C./16 hr. MAb/1-8C6 was diluted in TPBS (phosphate buffered saline containing a detergent, Tween-20) so as to give an $A_{490}$/10min value of 1.5–2.0. This dilution of antibody was mixed with the standard (Bβ 1-118) or any other desired competitor, and added to the plate. After washing, the amount of MAb/1-8C6 bound to the solid phase was detected using the enzyme anti-immunoglobulin conjugate, substrate and chromogen solutions described earlier (see Example 3). In these assays, Bβ 1-118, N-DSK and intact fibrinogen were found to react with MAb/1-8C6. (T)N-DSK, Aα 1-51 and γ 1-78 did not react despite the fact that solutions of each used for the assay were about 100 x molar excess in comparison to Bβ 1-118, N-DSK or intact fibrinogen. Identical results were obtained on ELISA using plates coated with either N-DSK or intact fibrinogen.

In the radioimmunoassay, the ligand was $^{125}$I-Bβ 1-118. The latter was prepared using the procedure described for the iodination of the Bβ 15-42 peptide from human fibrinogen (Kudryk et al., supra, 1982). Bound ligand was separated using Sac-Cel (donkey anti-mouse cellulose suspensions) following the suggestions outlined by the manufacturer (Wellcome Diagnostics, Research Triangle Park, NC). The radioimmunoassay consisted of four compartments and included two separate incubation periods. The assay procedure was almost identical to that recently described (Kudryk et al., supra, 1982), the exceptions being the ligand and second antibody as indicated earlier.

Appropriate dilutions of MAb/1-8C6 and Sac-Cel could bind almost 90% of the $^{125}$I-Bβ1-118 ligand. In the radioimmunoassay, dilutions of these reagents were selected so as to give about 40% binding of ligand in absence of any cold competitor. In these experiments, non-specific binding of the ligand did not exceed 5% when buffer or IgG isolated from a control clone culture fluid was substituted for MAb/1-8C6. Specific binding of the ligand was progressively inhibited by increasing quantities of 'cold' Bβ 1-118. As shown in FIG. 4, 50% inhibition of ligand binding was obtained at a concentration of approximately $5 \times 10^{-9}$M. Fibrinogen, N-DSK and (B)N-DSK all showed strong competition. In FIG. 4, N-DSK appears to be a somewhat weaker competitor by comparison with intact fibrinogen and (B)N-DSK. However, in subsequent experiments, using different lots of N-DSK, inhibition curves coincident with fibrinogen and (B)N-DSK were obtained (not shown). By contrast, (T)N-DSK, in the concentration range given in FIG. 4, did not compete and, therefore, was not bound by MAb/1-8C6. This was observed with every lot of (T)N-DSK tested. Slight competition with (T)N-DSK was detected, but only at a concentration greater than $10^{-6}$M.

Figure 5:
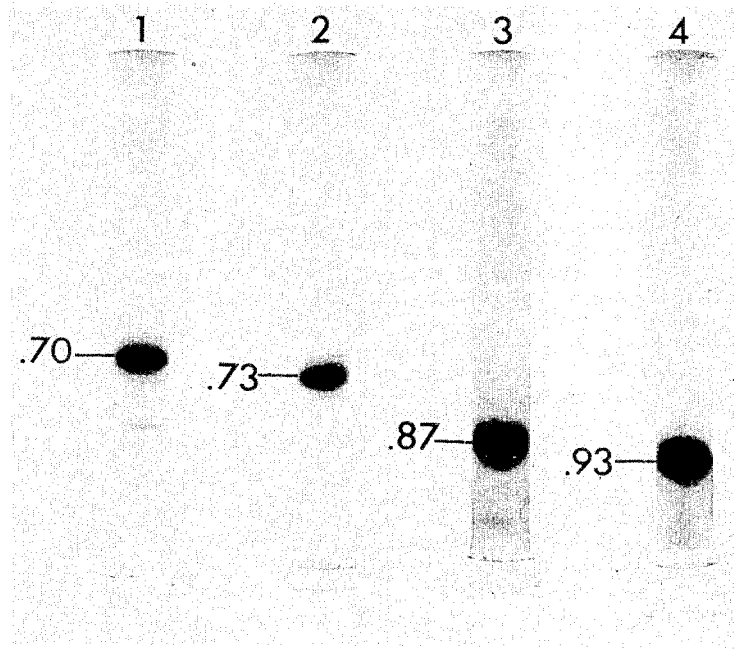
FIG. 5 depicts electrophoretic patterns of Bβ 1-118 before (gel 1 and 3) and after (gel 2 and 4) digestion with thrombin. Gels 1 and 2 were 10% acrylamide while gels 3 and 4 were 7% acrylamide in SDS. The mobility of the Bβ chain of each gel is indicated.
Figure 6:
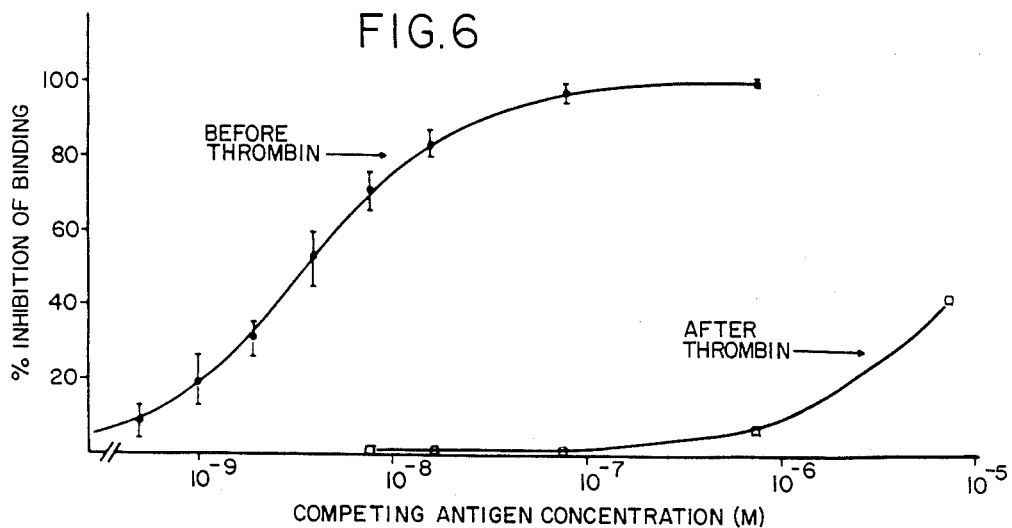
FIG. 6 is a graph depicting inhibition of binding of $^{125}I$-Bβ 1-118 ligand by standard amounts of "cold" Bβ 1-118 before and after thrombin digestion. Antibody dilution, specific and non-specific binding were as described in FIG. 4. The mean of eight (8) consecutive experiments is shown and the standard deviation is indicated by vertical bars.

Due to the known specificity of thrombin and the difference in reactivity between Bβ 1-118 and (T)N-DSK with MAb/1-8C6, Bβ 1-118 was digested with thrombin for use as a competitor in the radioimmunoassay. As shown in FIG. 5, a definite change in mobility was found for Bβ 1-118 after thrombin cleavage. This was observed both on 7 and 10% acrylamide gels in SDS. This change in mobility is consistent with the findings reported by Hessel et al., supra, 1979, and reflects the cleavage of the Bβ 14 Arg-15 Gly bond by thrombin. FIG. 6 depicts the competition curves obtained with Bβ 1-118 before and after thrombin digestion. As can be seen, approximately 2000 molar excess of the digested chain was required to achieve the same inhibition obtained with non-digested Bβ 1-118. Pure FPB, Bβ 15-42 or mixtures of the two peptides did not compete in the radioimmunoassay in the concentration range shown in FIG. 6.

The difference in reactivity with Bβ 1-118 and that when it is part of a multi-chain structure may be due to the fact that the epitope to which MAb/1-8C6 is directed is fully reactive only when it is surface-oriented on fibrinogen and related disulfide-bonded fragments.

As shown in FIG. 6, most of the Bβ 1-118 reactivity was lost when the chain was digested with thrombin. This result, coupled with the fact that (T)N-DSK, free Bβ 1-14 (FPB) as well as Bβ 15-42 failed to react with MAb/1-8C6, clearly shows that this antibody is directed to an epitope in or around the thrombin susceptible Bβ 14 Arg-15 Gly bond. When the latter is completely cleaved with thrombin, all immunoreactivity by Bβ 1-118 and related structures is abolished.

Example 5

Specificity of MAb/T2G1s

The specificity of MAb/T2G1s was tested by the ELISA method. Microtiter plates were coated with (T)N-DSK (0.8 μg/ml) at +4° C./16 hours. MAb/T2G1s was diluted in TPBS so as to give an $A_{490}$/5 min value of about 1.6. This dilution of antibody was mixed with dilutions of the desired competitor and added to the plate. After washing, the antibody bound to the solid phase was detected as described above (see Example 3).

Figure 10:
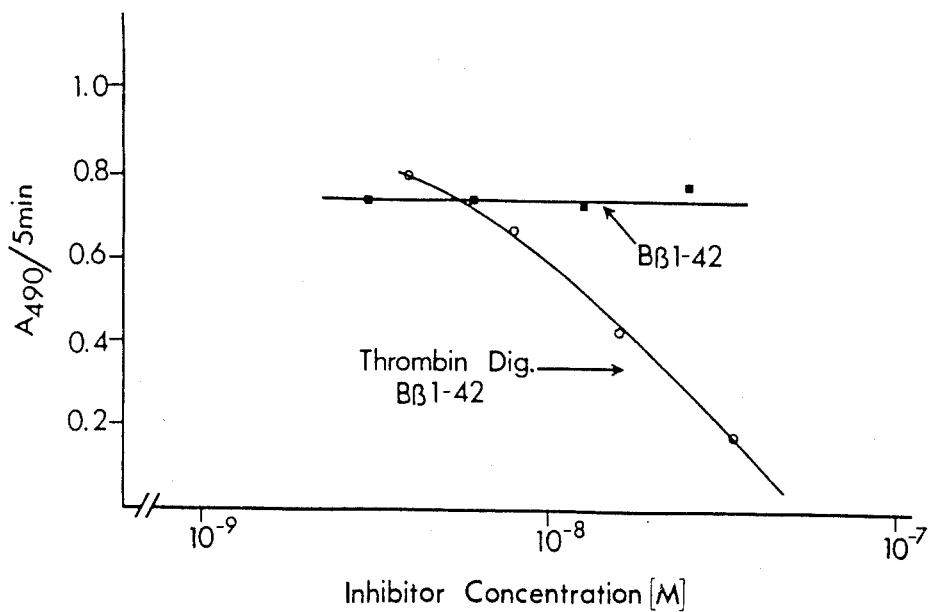
FIG. 10 is a graph depicting competition ELISA using a (T)N-DSK-coated plate (0.8 μm/ml) and MAb/T2G1s. The inhibitors were Bβ1-42 before and after digestion with thrombin. The $A_{490}$/5 min values in buffer control wells (no inhibitor added) was about 0.8.

The ELISA, MAb/T2G1s reacted strongly with (T)N-DSK coated plates. Since this antibody also bound the $^{125}$I Bβ15-42 ligand in solution, attempts were made to coat the peptide on plates and demonstrate that MAb/T2G1s would bind such plates. In these experiments, stock solutions [0.05–0.1 μg/ml] of the Bβ15-42 peptide were made in coupling buffer described above. Plates coated with these solutions were shown to specifically bind MAb/T2G1s. Similar results were obtained on plates coated with thrombin-digested Bβ1-42. MAb/T2G1s did not bind to plates coated with Bβ1-42. FIG. 10 shows the results of a competitive ELISA experiment using (T)N-DSK coated plates and MAb/T2G1s. The competitors used were Bβ1-42 before and after digestion with thrombin. The BB15-42 peptide gave a competition curve similar to that observed with thrombin-digested Bβ1-42.

A radioimmunoassay was also employed in order to check the specificity of MAb/T2G1s. The ligand utilized was $^{125}$I Bβ15-42. The latter was prepared using the procedure already described (Kudryk et al., supra, 1982). Bound ligand was separated using Sac-Cel (donkey anti-mouse immunoglobulin cellulose suspensions) following the suggestions outlined by the manufacturer (Wellcome Diagnostics, Research Triangle Park, NC). The radioimmunoassay consisted of four compartments and included two separate incubation periods and was almost identical to that recently described (Kudryk et al., supra, 1982), the exception being the specific [MAb/T2G1s] and second antibody as indicated above.

Figure 11:
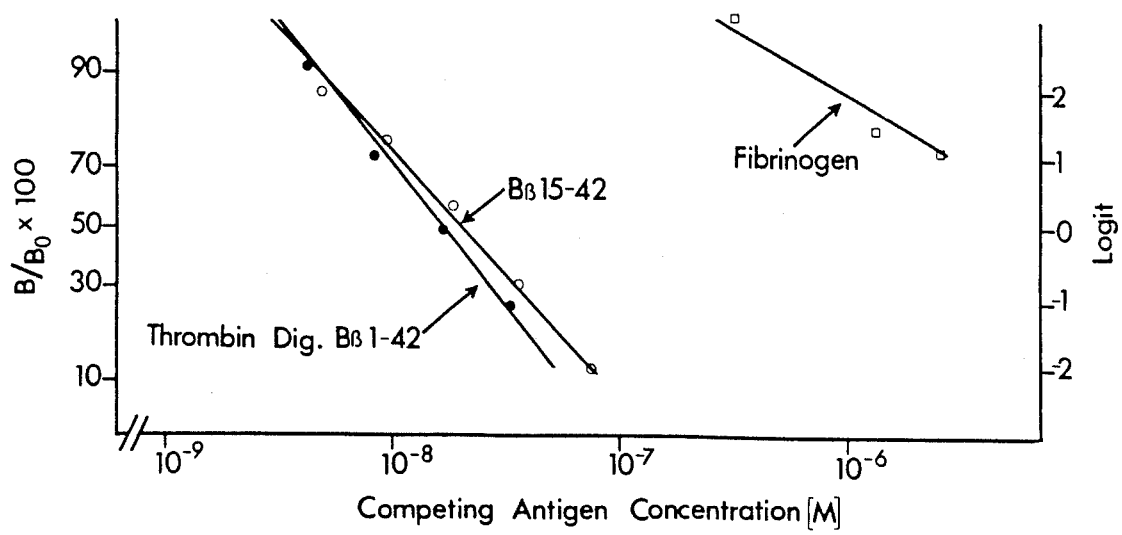
FIG. 11 is a graph depicting inhibition of binding $^{125}I$ Bβ15-42 ligand to MAb/T2G1s by the indicated "cold" competitors. (T)N-DSK gave an inhibition curve which was identical to that shown with Bβ15-42 or thrombin digested Bβ1-42. Intact Bβ1-42, Bβ1-118, N-DSK and (B)N-DSK did not cross-react in the concentration range shown. Slight competition was observed using normal human plasma but only when added in very low dilution.

Appropriate dilutions of the antibody and second antibody (Sac-Cel) were selected so as to give about 40% binding of the $^{125}$I B$\beta$15-42 ligand in absence of a competitor. As shown in FIG. 11, binding of this ligand was inhibited by increasing quantities of "cold" B$\beta$15-42 standard. The 50% displacement level was obtained at a concentration of about $2\times10^{-8}$M. Similar inhibition was observed with thrombin digested BB1-42 and (T)N-DSK (not shown). Intact B$\beta$1-42, N-DSK and (B)N-DSK showed little, if any, inhibition. Different lots of IMCO fibrinogen showed slight inhibition. However, the molar ratios comparing maximum displacement of ligand for B$\beta$15-42 against that of intact fibrinogen was on the order of 1:250.

Based on the data shown in FIG. 10 and FIG. 11, the above results are interpreted in the following manner. Since FPB is part of B$\beta$1-42 and is missing from both (T)N-DSK and B$\beta$15-42, it would appear that immunoreactivity between MAb/T2G1s and fibrinogen or its fragments requires a prior cleavage of the bond B$\beta$ 14-Arg 15 Gly in all the antigens.

As shown in FIG. 11, a slight but measurable cross-section was detected with MAb/T2G1s and intact fibrinogen. As already mentioned, this was observed with several different lots of IMCO fibrinogen. One explanation for this is that such fibrinogen preparations contain some small quantity of fibrin which remain in solution as a fibrinogen-fibrin complex [Shainoff & Page, 1962]. In support of this is the fact that NH$_2$-terminal analyses on such preparation almost always show small amounts of glycine. This amino acid is the new NH$_2$-terminal residue when both FPA and FPB are released as consequence of thrombin action [Blombäck & Yamashina, 1958].

As described in Example 4, MAb/1-8C6 completely cross-reacted with intact fibrinogen. Because MAb/T2G1s reacted only slightly with different fibrinogen preparations, such reactions were probably due to trace contamination by fibrin. In order to compare the difference in reactivity of these two antibodies towards fibrinogen, a very simple experiment was designed using fibrinogen-coated ELISA plates. In preparation of fibrinogen and fibrin-coated ELISA plates, IMCO fibrinogen (Lot F-155, 4.3 mg/ml) was diluted 1/500 in Na$_2$CO$_3$/NaHCO$_3$, pH 9.6 and coated onto polyvinyl microtiter plates at +4° C./16 hours. After washing, "blocking" with 5% BSA [RIA-grade BSA, Sigma, St. Louis, MO] an subsequent washing, 100 $\mu$l of human thrombin [Sigman, St. Louis, MO] stock solution (1 NIH unit/ml in n-saline) was added to each well. At selected intervals, thrombin was inhibited by adding an equal volume of the D-Phe-Pro-Arg-CH$_2$Cl stock solution given above. Subsequent washings, reactions and detection of bound antibody were identical to that already described.

Figure 12:
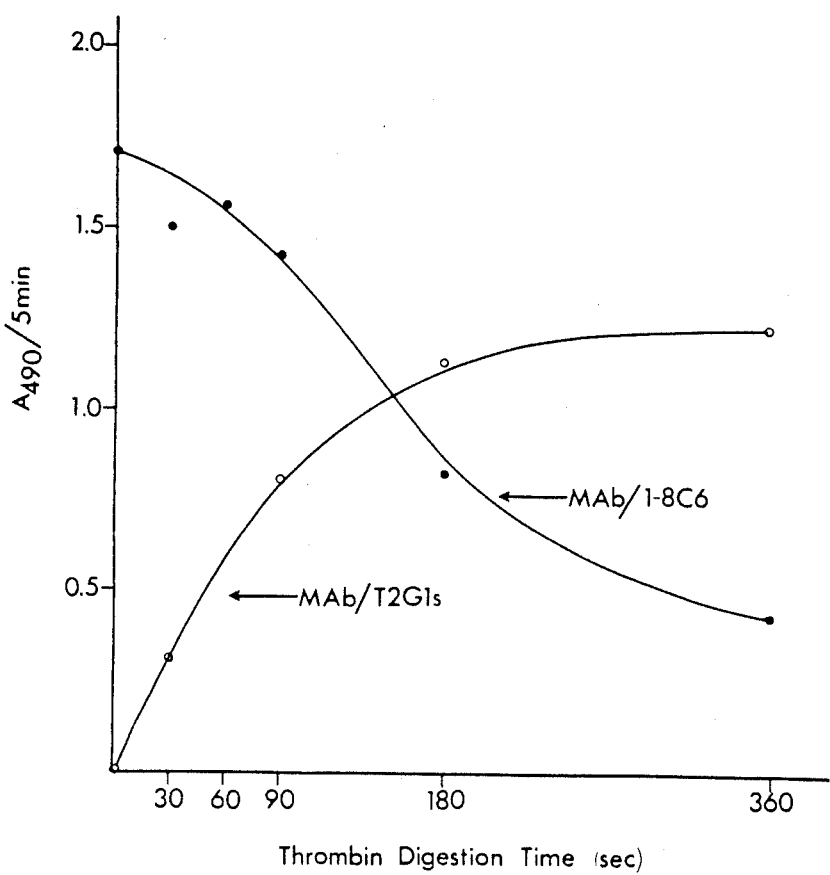
FIG. 12 is a graph depicting reactivity of two different monoclonal antibodies on fibrinogen-coated ELISA plates following thrombin digestion. The experiment was conducted on a single (96 well) plate to which thrombin was added. Digestion—at the indicated time—was terminated by addition of the thrombin inhibitor D-Phe-Pro-Arg-$CH_2Cl$. The $A_{490}$/5 min value for MAb/1-8C6 on control (non-digested) fibrinogen-coated plates was about 1.7. On identical plates, MAb/T2G1s only gave background color.

As shown in FIG. 12, significant A$_{490}$/5 min values were obtained with MAb/1-8C6 when it was added to fibrinogen-coated wells which had been treated with a thrombin solution for 90 seconds or less. When this antibody was added to wells treated with thrombin for periods longer than 90 seconds, a sharp decrease in color resulted which meant a decrease in antibody binding. The completely predictable reverse result was obtained with MAb/T2G1s. Only background color was observed when this antibody was added to non-treated wells. However, with increasing time of exposure to thrombin, highly significant A$_{490}$/5 min values were recorded. These results suggest that thrombin digestion progressively exposed a neoepitope on the surface of the ELISA plate and that MAb/T2G1s was able to react with and bind to this neoepitope.

Example 6

Clinical Applications of MAb/1-8C6

Once the specificity of MAb/1-8C6 was established, it was of interest to study its usefulness in clinical investigation. For this purpose, blood was collected from uremic patients at selected intervals during hemodialysis. The collection and processing were identical to that already described (Kudryk et al., Thromb. Res., 25, 277–291, 1982). In order to remove the last traces of fibrinogen, lyophilized ethanol extracts of patient plasma were further purified on disposable Sep-Pack C$_{18}$ cartridges (Waters Associates, Milford, MA) according to the method of Koehn and Canfield, Analyt. Biochem, 116, 349–456, 1981.

In previous experiments it was determined that such patients had very high levels of B$\beta$ 15-42 immunoreactive material, as much as 40 or more times the 0.41 pmoles/ml found in normal subjects (Kudryk et al., supra, 1982). In the present study it was of interest to setermine what percent, if any, of the B$\beta$ 15-42 immunoreactive material normally found in this patient group would cross-react with MAb/1-8C6.

Since fibrinogen reacts with MAb/1-8C6(FIG. 4), patient plasma extracts prepared by methods described previously (Kudryk et al., supra, 1982) were further purified on Sep-Pak C$_{18}$ cartridges. Later, the samples were split into two fractions and one of these was digested with thrombin (90 NIH units/ml at 37° C./60 min). Finally, appropriate dilutions of each sample were made and used in the radioimmunoassay as described in Example 4.

Table 1 shows the plasma concentration of fibrinogen, FPA and B$\beta$ 15-42 immunoreactive material in three patients. Samples were taken prior to and at two different time points in the dialysis program. The latter two samples were from the venous (outlet side) blood line. The FPA concentraiton in the pre-dialysis sample from each patient gave slightly higer values than the 1.4±0.6 pmoles/ml level found in normal subjects using the IMCO assay kit (Wilhelmsson et al., Clin. Nephrol., 15, 252–258, (1981).

TABLE 1
Plasma levels of fibrinogen and degradation products in three hemodialysis patients.

| Patient (diagnosis) | Blood sampling time[1] | Fibrinogen[2] (mg/ml) | FPA[3] (pmol/ml) | Bβ 15-42 immunoreactivity[4] (pmol/ml) | Bβ 15-42 immunoreactivity detected with MAb/1-8C6[5] (pmol/ml) |
|---|---|---|---|---|---|
| 589 (polycystic kidney) | I | 1.8 | 3.5 | 41.1 | 32.3 |
|  | II | 2.5 | 1.8 | 49.0 | 72.7 |
|  | III | 2.8 | 4.0 | 58.3 | 50.5 |
| 172 (nephrosclerosis) | I | 4.5 | 2.6 | 35.5 | 38.7 |
|  | II | 4.8 | 4.0 | 36.6 | 26.8 |
|  | III | 4.7 | 7.3 | 37.7 | 40.7 |
| 539 (chronic glomerulonephritis) | I | 4.2 | 2.2 | 10.5 | 7.1 |
|  | II | 4.6 | 1.3 | 11.5 | 10.4 |
|  | III | 3.6 | 2.0 | 14.1 | 7.7 |

[1]Blood samples were taken prior to dialysis (I), two hours into dialysis (II) and just before each patient was disconnected from the dialyzer, approximately 3 hours later (III). Sample I was drawn through the arterial fistula needle. The other two samples were taken by puncture of the venous (outlet side) blood line.
[2]Determined by electroimmunoassay as described previously (Kudryk et al., 1982).
[3,4]Measured by the FPA and Bβ 15-42 radioimmunoassay kits purchased from IMCO Corporation Ltd., Stockholm, Sweden. The procedure for each assay was that recommended by the manufacturer.
[5]The radioimmmunoassay was that described in Materials and Methods. Human Bβ 1-118 was used as both ligand and standard and the anitbody was MAb/1-8C6.

A drop in FPA was observed in sample 2 in two of the three patients. The last sample from all three patients gave higher values as compared to sample 2.

These results are consistent with previous findings which showed that FPA was normal or near normal during the early stages of dialysis when heparin levels were greater than 0.5IU/ml. When heparin fell below this value, increases in FPA concentration were generally observed (Wilhelmsson et al., supra, 1981). The efficiency of heparin therapy can be checked in this manner. For example, an elevation in plasma levels of FPA can be taken as an index of high thrombin activity which may result in intravascular fibrin deposition.

Regarding Bβ 15-42 immunoreactivity, the level detected with the rabbit antiserum was significantly higher than the 0.41 pmoles/ml found in normal plasma (Kudryk et al., supra, 1982). Patient 172 showed very similar concentration in all three samples. This was not the case for the other two patients, especially when the pre-dialysis and sample 3 levels were compared. The concentration of Bβ 15-42 immunoreactive material detected with MAb/1-8C6 was similar but not identical to that found using the rabbit antiserum. From the specificity of MAb/1-8C6 described earlier, these results suggested that most but not all the Bβ 15-42 immunoreactive material was present on a peptide or peptides which contain an intact Bβ 14 Arg-15 Gly bond. This was verified in part when each sample was digested with thrombin and reassayed using both systems. The concentration of Bβ 15-42 immunoreactive material detected with the rabbit antiserum was similar before and after thrombin digestion. On the other hand, very little, if any, immunoreactive material could be measured with MAb/1-8C6 in the thrombin digested samples (data not shown).

Figure 7A:
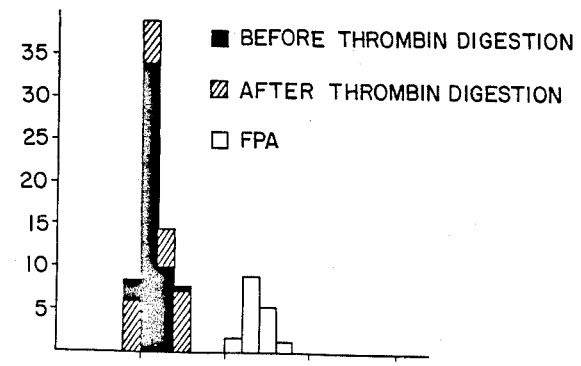
FIG. 7a, FIG. 7b and FIG. 7c are graphs depicting immunoreactivity profiles on fractions obtained from a high-performance chromatography run using an extract made from pooled (5.7 ml) patient plasma. The column and conditions were similar to those described in FIG. 2. Following chromatography, acetonitrile was removed by evaporation and each fraction was dissolved in 1.0 ml 0.2M $NH_4HCO_3$ and used for immunoassay. Only fractions 5-8 were analyzed before and after thrombin digestion. FPA was measured on samples before thrombin digestion only. Top panel: immunoreactivity using the commercial Bβ 15-42 radioimmunoassay kit [IMCO Corporation, Ltd., Stockholm, Sweden]; middle panel: immunoreactivity measured with MAb/1-8C6; bottom panel: FPB immunoreactivity of fractions 5-8 after thrombin only. The FPB was found in fractions 5-8 and 17-19.
Figure 7B:
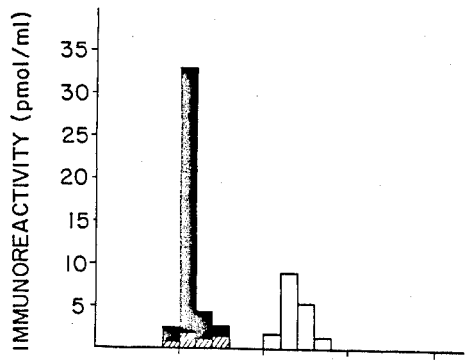
Figure 7C:
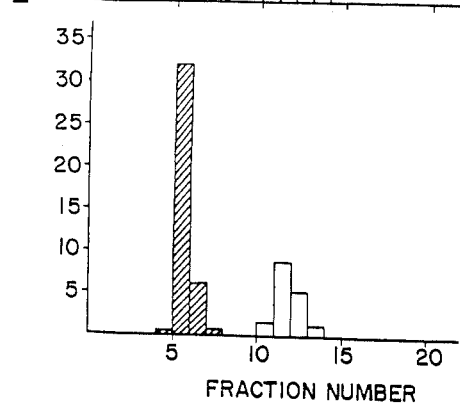
Figure 8:
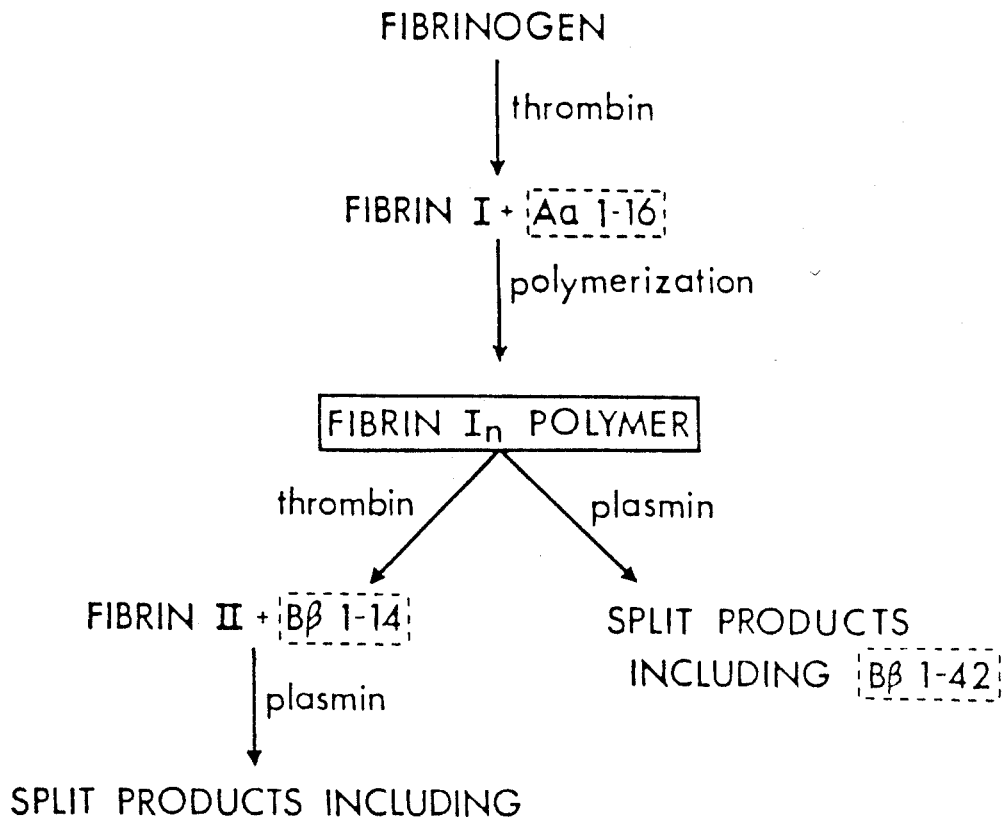
FIG. 8 depicts a scheme of in vivo fibrinogen proteolysis by thrombin and plasmin as postulated by Nossel and collaborators (adapted from Nossel et al., *J. Clin. Invest.*, 64, 1371–1378, 1979).

In order to further characterize the nature of the in vivo degradation products, an extract was prepared from pooled patient plasma. The plasma used was from several patients, excluding those listed in Table 1, and was collected at different times during dialysis. The extract was fractionated by high-performance liquid chromatography as described by Koehn and Canfield, Analyt. Biochem, 116, 349–356, 1981. The fractions were later assayed for FPA as well as Bβ 15-42 immunoreactivity. Those fractions showing high Bβ 15-42 activity were digested with thrombin and later reanalyzed using both Bβ 15-42 assays as well as the FPB immunoassay. As shown in FIG. 7, FPA was recovered in fractions 11–14. Bβ 15-42 immunoreactivity was detected in fractions 5–8 using both the rabbit antisera and MAb/1-8C6. When each fraction was digested with thrombin and reassayed, very little, if any, change in immunoreactivity was observed with the rabbit antibody. In contrast, major differences were obtained on the thrombin-digested fractions using the other two assays. Virtually all immunoreactivity with MAb/1-8C6 was lost. Significant levels of FPB immunoreactivity were obtained in fraction 5–8 only after thrombin digestion. It should also be pointed out that some FPB immunoreactivity was detected in fractions 5–8 and 17–19 prior to digestion with thrombin.

From the specificity of MAb/1-8C6 already discussed, these results suggest that most of the Bβ 15-42 immunoreactive material was present on peptides which contained FPB. The data shown in FIG. 7 also support this conclusion. That is, peptides eluting much ealier than free FPB specifically reacted with the FPB antiserum. Therefore, such peptides could only have originated from fibrinogen or fibrin I but not fibrin II. Several additional comments need be made concerning the data presented in Table 1 and FIG. 7. Regarding the level of immunoreactive material detected with the rabbit antiserum and MAb/1-8C6, sample 2 from patient 589 shows that a significantly higher amount was measured with the monoclonal antibody. One explanation for this is that some Bβ 15-42 immunoreactive material which could normally be detected by the rabbit antiserum was lost during sample preparation. It has already been shown that the Bβ 15-42 standard undergoes rapid decay when added to normal or patient serum (Kudryk et al., supra, 1982). A number of immunoreactivity profiles have been obtained on high-performance liquid chromatography fractions with the three Bβ chain related assays described in this study. The one shown in FIG. 7 was from an experiment using an extract from pooled patient plasma. Chromatography of other samples gave quite different results. In some, Bβ chain immunoreactivity was also located in fractions eluting near free FPA. From these results it is clear that such patients have a number of peptides which can cross-react with the antibodies described in this report. The identification of the precise molecular nature of these in vivo peptides is now being investigated. Finally, some comment on the very high level of Bβ 15-42 immunoreactive material in these patients must be made. Since FPA concentrations were normal or near normal in samples 1 and 2, it seems clear that fibrin formation was effectively controlled in all three patients by the heparin regimen which was employed. With this in mind, as well as the fact that even the pre-dialysis levels of Bβ 15-42 immunoreactive material were so significantly elevated, the question of impaired catabolism of these degradation products must be considered. In this regard, Sherman and collaborators studied turnover of much larger fibrinogen degradation products in several animal models. Their results suggested that loss of functioning renal tissue rather than uremia per se was responsible for decreased clearance of fibrinogen degradation products (Hayne and Sherman, Am. J. Path., 71, 219–236, 1973; Iio et al., J. Lab. Clin. Med., 87, 934–946, 1976). As seen in Table 1, some patients show a steady increase of these peptides during dialysis. This cold result from fibrinogenolysis which, in its early stages, would not be accompanied by increases in FPA concentration (Bilezikian et al., J. Clin. Invest., 56, 438–445, 1975).

On the basis of the above data, we conclude that MAb/1-8C6 serves as a useful reagent in clinical studies on disease states associated with fibrino(geno)lysis. Important information regarding the nature of in vivo generated fibrin and the kinetics of its dissolution may be obtained by using immunoassays which measure the Bβ chain marker discussed above.

Example 7

Determining the presence of Bβ 1-42 and Bβ 15-42 in clinical test specimens

Blood is collected from patients by flawless venipuncture with 1.4 mm needle. After discarding the first 2-3 ml, the subsequent 9 ml of blood is allowed to run directly into a 12 ml polystyrene tube with 1 ml 0.15 M NaCl containing 1000 IU heparin and 1000 KIU Trasylol. The tube is immediately inverted 3 times against a plastic film and centrifuged at 3000–3500 g, 4° C., 20 minutes. Each plasma sample is processed directly or is stored at −70° C. Frozen plasma samples are quickly thawed at 37° C. and then processed immediately as described. The plasma processing is performed as follows. To 1.0 ml plasma in a 3 ml plastic tube 1.0 ml of chilled (ice-bath) ethanol is added. After mixing and incubation in an ice-bath for 30 minutes the sample is centrifuged as above. The supernatant is transferred to a new centrifuge tube and kept in an ice-bath for an additional 30 minutes and re-centrifuged. The second supernatant is the "processed plasma sample."

In order to remove the last traces of fibrinogen from the "processed plasma sample," the latter are further purified on disposable Sep-Pak $C_{18}$ cartridges (Waters Associates, Milford, MA) according to the method of Koehn and Canfield, Analyt. Biochem., 116, 349–356 (1981).

Each "processed plasma sample" is tested by competitive immunoassays: enzyme linked immunoassay (ELISA) or radioimmunoassay (RIA). The "processed plasma sample" can be split into two fractions, one which is used to detect the presence of Bβ 1-42, and one which is used to detect the presence of Bβ 15-42. In order to test for the presence of Bβ 1-42 antigen using ELISA, microtiter plates are coated with, e.g., Bβ 1-42 antigen or Bβ 1-118 (5 µg/ml) at +4° C./16 hours. MAb/1-8C6 is diluted in TPBS (phosphate buffered saline containing a detergent, Tween-20) to give an $A_{490}$/10 min. value of 1.5–2.0. This dilution is mixed with dilutions of the "processed plasma sample" and added to the plate. After incubation and washing, the antibody bound to the solid phase is detected as described earlier (see Example 3).

To test for the presence of Bβ 15-42 antigen using ELISA, microtiter plates are coated with Bβ 15-42 at 4° C./16 hr.. MAb/T2G1s is diluted in TPBS to give an $A_{490}$/5 min value of about 1.6. This dilution of antibody is mixed with dilutions of the "processed plasma sample" and added to the plate. After incubation and washing, the antibody bound to the solid phase is detected as described above (see Example 3).

To test the "processed plasma sample" for the presence of Bβ 1-42 antigen using RIA, the procedure described above (see Example 4) is followed. The ligand is $^{125}I$ - Bβ 1-42 or $^{125}I$ - Bβ 1-118, the antibody is MAb/1-8C6 and the second antibody is donkey antimouse antibody suspended in cellulose, i.e., Sac-Cel). (see Example 4).

To test for the presence of Bβ 15-42 antigen using RIA, the same procedure described above is followed. The ligand is $^{125}I$-Bβ 15-42, the antibody is MAb/T2G1s and the second antibody is Sac Cel.

The present invention may be embodied in other specific forms without departing from the spirit or essential attributes thereof and, accordingly, reference should be made to the appended claims, rather than the foregoing specification as indicating the scope of the invention.

What is claimed is:

1. A monoclonal antibody wherein said antibody:
  (a) binds wih a peptide fragment of the Bβ chain of human fibrinogen or human fibrin I containing amino acid residues 1-42 of said Bβ chain;
  (b) does not bind with a peptide fragment of the Bβ chain of human fibrinogen or human fibrin I containing amino acid residues 1-14; and
  (c) does not bind with a peptide fragment of the Bβ chain of human fibrinogen or human fibrin I containing amino acid resides 15-42.

2. In a process for detecting the presence of an $NH_2$-terminal fragment of an Bβ chain of human fibrinogen or human fibrin, said fragment containing at least amino acid residues 1-42 of the BB chain of human fibrinogen or human fibrin I, in a plasma sample by enzyme linked immunosorbent assay or radioimmunoassay by contacting said sample with an antibody which bonds to an $NH_2$-terminal fragment of the Bβ chain of human fibrinogen or human fibrin I, said fragment containing at least amino acid residues 1-42 of the Bβ chain of human fibrinogen or human fibrin I and detecting immunoreaction, the improvement wherein said antibody is the antibody of claim 1.

3. A process according to claim 2, wherein said antibody is mixed with said sample in the presence of a radioactively labeled fragment of the Bβ chain of human fibrinogen or human fibrin I containing amino acid residues 1-42 and the radioactively labeled fragment bound to said antibody is separated using an antibody specific to said antibody.

4. A process according to claim 2, wherein said antibody is mixed with said sample, the mixture contacted with a polypeptide fragment of the Bβ chain of human fibrinogen or human fibrin I containing amino acid residues 1-42 and an antibody specific to said antibody is enzyme linked.

5. A process according to claim 2, wherein an enzyme linked immunosorbent assay is performed.

6. A process according to claim 3, wherein a radioimmunoassay is performed.

7. A process according to claim 2, wherein the results of said enzyme linked immunosorbent assay or said radioimmunoassay are compared with a known standard to determine the relative concentration of antigen in the test specimen as compared to a normal sample.

8. A kit for determining whether the plasma contained in a test sample includes a particular peptide fragment of human fibrin I or human fibrinogen, comprising,
   (i) the monoclonal antibody of claim 1
   (ii) an $NH_2$-terminal peptide fragment of the Bß chain of humam fibrinogen or human fibrin I containing amino acid residues 1-42,
   (iii) human fibrinogen, and
   (iv) an enzyme-linked immunoglobulin specific to animal immunoglobulin, said antibody, said $NH_2$-terminal peptide fragment, human fibrinogen and enzyme-linked immunoglobulin all being present in amounts sufficient to perform an assay for said peptide fragment of human fibrin I or human fibrinogen.

9. A process for determining the amount of a peptide fragment of the B beta chain of human fibrinogen or human fibrin I present in a plasma sample, said fragment containing amino acid residues 1-42, which comprises:
   (a) contacting said sample with known amounts of a monoclonal antibody according to claim 1, a competitive antigen on a solid support, which competitive antigen comprises an $NH_2$-terminal peptide fragment of the Bß chain of human fibrinogen or human fibrin I comprising amino acid residues 1-42 and an enzyme-linked antibody, which antibody binds to mouse immunoglobulin;
   (b) detecting the amount of said monoclonal antibody bound to the competitive antigen on the solid support by determining the amount of bound enzyme-linked antibody; and
   (c) comparing the results of steps (a) and (b) with that obtained using a standard amount of known antigen comprising an $NH_2$-terminal peptide fragment of the Bß chain of human fibrinogen or human fibrin I comprising amino acid residues 1-42.

10. A process for determining the amount of an $NH_2$-terminal peptide fragment of the Bß chain of human fibrinogen or human fibrin I, present in a plasma sample, said fragment containing amino acid residues 1-42, comprising:
    (a) contacting said sample with known amounts of each of a monoclonal antibody according to claim 1 and a competitive radio-labeled antigen comprising an $NH_2$-terminal peptide fragment of the BB chain of human fibrinogen or human fibrin I comprising amino acid residues 1-42, such that the competitive radio-labeled antigen can bind with the monoclonal antibody;
    (b) contacting said sample, said monoclonal antibody and said competitive radio-labeled antigen of step (a) with an antibody specific to mouse immunoglobulin;
    (c) separating the antibody bound radio-labeled antigen of step (b) using the antibody of step (b);
    (d) counting the radioactivity of the bound radio-labeled antigen of step (c); and
    (e) comparing the results of steps (a), (b), (c) and (d) with that obtained using a standard amount of known antigen comprising an $NH_2$-terminal peptide fragment of the Bß chain of human fibrinogen or human fibrin I comprising amino acid residues 1-42.

11. A monoclonal antibody wherein said antibody:
    (a) binds with a peptide fragment of the Bß chain of human fibrin II containing amino acid residues 15-42 of said Bß chain;
    (b) does not bind with an $NH_2$-terminal peptide fragment of the Bß chain of human fibrinogen or human fibrin I containing amino acid residues 1-14;
    (c) does not bind with an $NH_2$-terminal peptide fragment of the Bß chain of human fibrinogen or human fibrin I containing amino acid residues 1-42.

12. A monoclonal antibody according to claim 11 wherein the monoclonal antibody binds with the products produced by thrombin digestion of human fibrinogen but does not bind with the product resulting from thrombin digestion of rabbit fibrinogen.

13. In a process for detecting the presence of a fragment of the Bß chain of human fibrin II, said fragment containing at least amino acid residues 15-42 of the Bß chain of human fibrin II, in a plasma sample by enzyme linked immunosorbent assay or radioimmunoassay by contacting said sample with an antibody which binds to a fragment of the Bß chain of human fibrin II, said fragment containing at least amino acid residues 15-42 of the Bß chain of human fibrin II, and detecting immunoreaction, the improvement wherein said antibody is the antibody of claim 11.

14. A process according to claim 13, wherein said antibody is contacted with said sample in the presence of a radioactively labeled fragment of the Bß chain of human fibrin II containing amino acid residues 15-42 and the radioactively labeled fragment bound to said antibody is separated using an antibody specific to said antibody.

15. A process according to claim 13, wherein said antibody is mixed with said sample, the mixture contacted with a polypeptide fragment of the Bß chain of human fibrin II containing amino acid residues 15-42 and an antibody specific to said antibody is enzyme linked.

16. A process according to claim 13, wherein an enzyme linked immunosorbent assay is performed.

17. A process according to claim 13, wherein a radioimmunoassay is performed.

18. A process according to claim 13, wherein the results of said enzyme linked immunosorbent assay or said radioimmunoassay are compared with a known standard to determine the relative concentration of antigen in the test specimen as compared to a normal sample.

19. A process for determining the amount of a peptide fragment of the Bß chain of human fibrin II present in a plasma sample, said fragment containing amino acid residues 15-42 comprising:
    (a) contacting said sample with known amounts of each of a monoclonal antibody according to claim 11, a competitive antigen on a solid support comprising an $NH_2$-terminal a peptide fragment of the Bß chain of human fibrin II comprising amino acid residues 15-42 and an enzyme-linked antibody which binds to mouse immunoglobulin;
    (b) detecting the amount of said monoclonal antibody bound to the competitive antigen on the solid support by determining the amount of bound enzyme-linked antibody; and
(c) comparing the results of steps (a) and (b) with that obtained using a standard amount of known antigen comprising a peptide fragment of the Bβ chain of human fibrin II comprising amino acid residues 15-42.

20. A process for determining the amount of a peptide fragment of the Bβ chain of human fibrin II, present in a plasma sample, said fragment containing amino acid residues 15-42, comprising:
(a) contacting said sample with known amounts of each of a monoclonal antibody according to claim 11, a competitive radio-labeled antigen comprising a peptide fragment of the Bβ chain of human fibrin II comprising amino acid residues 15-42 such that the competitive radio-labeled antigen is bindable with the monoclonal antibody;
(b) contacting said sample, the monoclonal antibody, and the competitive radio-labeled antigen of step (a) with an antibody specific to mouse immunoglobulin;
(c) separating the antibody bound radio-labeled antigen of step (b) using the antibody of step (b);
(d) counting the radioactivity of the bound radio-labeled antigen of step (c); and
(e) comparing the results of steps (a), (b), (c) and (d) with that obtained using a standard amount of known antigen comprising a peptide fragment of the Bβ chain of human fibrin II comprising amino acid residues 15-42.

21. A process for removing fibrin II from the blood in the bloodstream of a patient comprising:
(a) immobilizing the monoclonal antibody of claim 11 on a solid support,
(b) placing said immobilized monoclonal antibody within a hemodialysis chamber at a location in the chamber before the blood is returned to the patient and
(c) effecting hemodialysis of said patient by passing the blood of said patient through said hemodialysis chamber such that said blood contacts said immobilized monoclonal antibody, for a time and under conditions to bind human fibrin II in the blood of said patient to said immobilized monoclonal antibody.

22. A process for detecting the potential for the onset of occlusive thrombosis in a patient comprising dividing a plasma sample from said patient into a first fraction and a second fraction and
(a) treating the first fraction by:
(i) contacting said first fraction with known amounts of each of a first monoclonal antibody,
(A) which binds with a peptide fragment of the Bβ chain of human fibrinogen or human fibrin I containing amino acid residues 1-42 of said Bβ chain;
(B) which does not bind with a peptide fragment of the Bβ chain of human fibrinogen or human fibrin I containing amino acid residues 1-14; and
(C) which does not bind with a peptide fragment of the Bβ chain of human fibrinogen or human fibrin I containing amino acid residues 15-42, a competitive antigen on a solid support, which competitive antigen comprises a peptide fragment of the Bβ chain of human fibrinogen or fibrin I comprising amino acid residues 1-42, and an enzyme-linked antibody which binds to mouse immunoglobulin;
(ii) detecting the amount of said first monoclonal antibody bound to the competitive antigen on the solid support by determining the amount of bound enzyme-linked antibody;
(iii) comparing the results of steps (i) and (ii) with that obtained using a standard amount of known antigen comprising a peptide fragment of the Bβ chain of human fibrinogen or human fibrin I comprising amino acid residues 1-42, in the first fraction;
(b) treating the second fraction by:
(i) contacting said second fraction with known amounts of each of a second monoclonal antibody, said second monoclonal antibody
(A) binds with a peptide fragment of the Bβ chain of human fibrin II containing amino acid residues 15-42 of said Bβ chain;
(B) does not bind with an NH₂-terminal peptide fragment of the Bβ chain of human fibrinogen or human fibrin I containing amino acid residues 1-14;
(C) does not bind with an NH₂-terminal peptide fragment of the Bβ chain of human fibrinogen or human fibrin I containing amino acid residues 1-42, a competitive antigen on a solid support, which competitive antigen comprises an NH₂-terminal peptide fragment of the Bβ chain of human fibrin II comprising amino acid residues 15-42, and an enzyme-linked antibody which antibody binds to mouse immunoglobulin
(ii) detecting the amount of said second monoclonal antibody bound to the competitive antigen on the solid support by determining the amount of bound enzyme-linked antibody;
(iii) comparing the results of steps (i) and (ii) with that obtained using a standard amount of known antigen comprising a peptide fragment of the Bβ chain of human fibrin II comprising amino acid residues 15-42, to determine the amount of a peptide fragment of the Bβ chain of human fibrin II comprising amino acid residues 15-42, in the second fraction;
(c) comparing the amount of peptide fragment of the Bβ chain of human fibrinogen or human fibrin I comprising amino acid residues 1-42 from step (a) (iii) with the amount of the peptide fragment of the Bβ chain of human fibrin II comprising amino acid residues 15-42 from step (b) (iii), thereby determining whether Bβ 15-42 predominates over Bβ 1-42, such predominance indicating said potential for the onset of occlusive thrombosis in said patient.

23. A process for detecting the potential for the onset of occlusive thrombosis in a patient comprising dividing a plasma sample from said patient into a first fraction and a second fraction and
(a) treating the first fraction by:
(i) contacting said first fraction with known amounts of each of a first monoclonal antibody
(A) which binds with a peptide fragment of the Bβ chain of human fibrinogen or human fibrin I containing amino acid residues 1-42 of said Bβ chain;
(B) which does not bind with a peptide fragment of the Bβ chain of human fibrinogen or human fibrin I containing amino acid residues 1-14; and (C) which does not bind with a peptide fragment of the Bβ chain of human fibrinogen or human fibrin I containing amino acid residues 15-42, and a competitive radio-labeled antigen comprising an NH$_2$-terminal peptide fragment of the Bβ chain of human fibrinogen or human fibrin I comprising amino acid residues 1-42, such that the competitive radio-labeled antigen is bindable with the first monoclonal antibody, (ii) contacting said first fraction, said first monoclonal antibody and said competitive radio-labeled antigen of step (i) with an antibody specific to mouse immunoglobulin;

(iii) separating the antibody bound radio-labeled antigen of step (ii) using the antibody of step (ii);

(iv) counting the radioactivity of the bound radio-labeled antigen of step (iii); and (v) comparing the results of steps (i), (ii), (iii) and (iv) with that obtained using a standard amount of known antigen comprising an NH$_2$-terminal peptide fragment of the Bβ chain of human fibrinogen or human fibrin I comprising amino acid residues 1-42 to determine the amount of a peptide fragment of the Bβ chain of human fibrinogen or human fibrin I comprising amino acid residues 1-42 in the first fraction;

(b) treating the second fraction by:

(i) contacting said second fraction with known amounts of a second monoclonal antibody, said second monoclonal antibody (A) binds with a peptide fragment of the Bβ chain of human fibrin II containing amino acid residues 15-42 of said Bβ chain;

(B) does not bind with an NH$_2$-terminal peptide fragment of the Bβ chain of human fibrinogen or human fibrin I containing amino acid residues 1-14;

(C) does not bind with an NH$_2$-terminal peptide fragment of the Bβ chain of human fibrinogen or human fibrin I containing amino acid residues 1-42, a competitive radio-labeled antigen comprising an NH$_2$-terminal peptide fragment of the Bβ chain of human fibrin II comprising amino acid residues 15-42, such that the competitive radio-labeled antigen is bindable with the second monoclonal antibody;

(ii) contacting said second fraction, said second monoclonal antibody and said competitive radio-labeled antigen of step (i) with an antibody specific to mouse immunoglobulin, (iii) separating the antibody bound radio-labeled antigen of step (ii) using the antibody of step (ii);

(iv) counting the radioactivity of the bound radio-labeled antigen of step (iii) and (v) comparing the results of steps (i), (ii), (iii) and (iv) with that obtained using a standard amount of known antigen comprising a peptide fragment of the Bβ chain of human fibrin II comprising amino acid residues 15-42 to determine the amount of a peptide fragment of the Bβ chain of human fibrin II comprising amino acid residues 15-42 in the second fraction and (c) comparing the amount of the peptide fragment of the Bβ chain of human fibrinogen or human fibrin I comprising amino acid residues 1-42 from step (a) with the amount of the peptide fragment of the Bβ chain of human fibrin II comprising amino acid residues 15-42 from step (b) (v), thereby determining whether Bβ 15-42 predominates over Bβ 1-42, such predominance indicating the said potential for the onset of occlusive thrombosis in said patient.

24. A kit for determining whether the plasma contained in a test sample includes a peptide fragment of human fibrin II, comprising, (i) the monoclonal antibody of claim 11, (ii) an NH$_2$-terminal peptide fragment of the Bβ chain of human fibrin II containing amino acid residues 15-42, (iii) human fibrin II and (iv) an enzyme-linked immunoglobulin specific to animal immunoglobulin, said antibody, said NH$_2$-terminal peptide fragment, said human fibrin II and said enzyme-linked immunoglobulin all being present in sufficient amounts to perform an assay for said peptide fragment for human fibrin II.

25. A kit for determining whether the plasma contained in a test sample includes a particular peptide fragment for human fibrin II, human fibrinogen or human fibrin I, comprising (i) a first monoclonal antibody (a) which binds with a peptide fragment of the Bβ chain of human fibrinogen or human fibrin I containing amino acid residues 1-42 of said Bβ chain;

(b) which does not bind with a peptide fragment of the Bβ chain of human fibrinogen or human fibrin I containing amino acid residues 1-14; and (c) which does not bind with a peptide fragment of the Bβ chain of human fibrinogen or human fibrin I containing amino acid residues 15-42, (ii) a second monoclonal antibody, said second monoclonal antibody (A) binds with a peptide fragment of the Bβ chain of human fibrin II containing amino acid residues 15-42 of said Bβ chain;

(B) does not bind with an NH$_2$-terminal peptide of the Bβ chain of human fibrinogen or human fibrin I containing amino acid residues 1-14;

(C) does not bind with an NH$_2$-terminal peptide fragment of the Bβ chain of human fibrinogen or human fibrin I containing amino acid residues 1-42, (iii) human fibrinogen, (iv) human fibrin II and (v) enzyme-linked immunoglobulins specific to animal immunoglobulin, said first monoclonal antibody, said second monoclonal antibody, said human fibrinogen, said human fibrin II and said enzyme-linked immunoglobulin all being present in sufficient amounts to perform an assay for said peptide fragments.

26. A monoclonal antibody according to claim 11, wherein said antibody is prepared by a method, which comprises the steps of:

(a) immunizing an animal with a solution comprising N-DSK;

(b) removing the spleen from each animal of step (a) and making a suspension of the cells from each spleen;

(c) fusing said cells of each spleen of step (b) with animal myeloma cells in the presence of a fusion promoter;

(d) diluting and culturing the fused cells from step (c) in separate wells in a medium which will not support the unfused myeloma cells;

(e) evaluating the supernatant in each well containing a hybridoma for the presence of antibodies to fibrinogen, N-DSK, or any related fragments thereof;

(f) selecting and cloning a hybridoma which produces antibody which reacts with a peptide fragment of the Bβ chain of human fibrinogen or fibrin I containing amino acid residues 1-42, but does not react with either of the peptide fragments of said Bβ chain containing amino acid residues 1-14 or 15-42; and (g) recovering the antibody from the supernatant of said clones.

27. A monoclonal antibody according to claim 26, wherein said animal is a mouse.

28. A monoclonal antibody according to claim 11 wherein said antibody is prepared by the method, which comprises the steps of:

(a) immunizing an animal with a solution comprising N-DSK;

(b) removing the spleen from each animal of step (a) and making a suspension of the cells from each spleen;

(c) fusing said cells of each spleen of step (b) with animal myeloma cells in the presence of a fusion promoter;

(d) diluting and culturing the fused cells from step (c) in separate wells in a medium which will not support the unfused myeloma cells;

(e) evaluating the supernatant in each well containing a hybridoma for the presence of antibodies to fibrinogen, N-DSK, or any related fragments thereof;

(f) selecting and cloning a hybridoma which produces antibody which reacts with a peptide fragment of the Bβ chain of human fibrinogen containing amino acid residues 1-42, but does not react with either of the peptide fragments of said Bβ chain containing amino acid residues 1-14 or 15-42;

(g) transferring said clones intraperitoneally into animals; and (h) harvesting the malignant ascites or serum from said animals, which ascites or serum contains the desired antibody.

29. A monoclonal antibody according to claim 28 wherein said animal is a mouse.

30. A method of preparing a monoclonal antibody, wherein said antibody:

(i) reacts with a peptide fragment of the Bβ chain of human fibrinogen or fibrin I containing amino acid residues 1-42 of said Bβ chain;

(ii) does not react with a peptide fragment of the Bβ chain of human fibrinogen or fibrin I containing amino acid residues 1-14; and (iii) does not react with a peptide fragment of the Bβ chain of human fibrinogen or fibrin I containing amino acid residues 15-42, said method comprising the steps of:

(a) immunizing an animal with a solution comprising N-DSK;

(b) removing the spleen from each animal of step (a) and making a suspension of the cells from each spleen;

(c) fusing said cells of each spleen of step (b) with animal cells in the presence of a fusion promoter;

(d) diluting and culturing the fused cells from step (c) in separate wells in a medium which will not support the unfused myeloma cells;

(e) evaluating the supernatant in each well containing a hybridoma for the presence of antibodies to fibrinogen, N-DSK, or any related fragments thereof, (f) selecting and cloning a hybridoma producing antibody which reacts with a peptide fragment of the Bβ chain of human fibrinogen or fibrin I containing amino acid residues 1-42 but does not react with either of the peptide fragments of said Bβ chain containing only amino acid residues 1-14 or 15-42, (g) transferring said clones intraperitoneally into animals; and (h) harvesting the malignant ascites or serum from said animals which ascites or serum contains the desired antibody.

31. A method of preparing a monoclonal antibody according to claim 30, wherein said animal is a mouse.

32. A method of preparing a monoclonal antibody, wherein said antibody:

(i) reacts with a peptide fragment of the Bβ chain of human fibrinogen or fibrin I containing amino acid residues 1-42 of said Bβ chain:

(ii) does not react with a peptide fragment of the Bβ chain of human fibrinogen or fibrin I containing amino acid residues 1-14; and (iii) does not react with a peptide fragment of the Bβ chain of human fibrinogen of fibrin I containing amino acid residues 15-42, said method comprising the steps of:

(a) immunizing an animal with a solution comprising N-DSK;

(b) removing the spleen from each animal of step (a) and making a suspension of the cells from each spleen;

(c) fusing said cells of each spleen of step (b) with animal myeloma cells in the presence of a fusion promoter;

(d) diluting and culturing the fused cells from step (b) in separate wells in a medium which will not support the unfused myeloma cells;

(e) evaluating the supernatant in each well containing a hybridoma for the presence of antibodies to fibrinogen, N-DSK or any related fragments thereof;

(f) selecting and cloning a hybridoma which produces antibody which reacts with a peptide fragment of the Bβ chain of human fibrinogen or fibrin I containing amino acid residues 1-42 but does not react with either of the peptide fragments of said Bβ chain containing amino acid residues 1-14 or 15-42; and (g) recovering the antibody from the supernatant of said clones.

33. A method of preparing a monoclonal antibody according to claim 123 wherein said animal is a mouse.

34. A monoclonal antibody according to claim 11, wherein said antibody is prepared by a method which comprises the steps of:

(a) immunizing an animal with a solution comprising (T)N-DSK;

(b) removing the spleen from each animal of step (a) and making a suspension of the cells from each spleen;

(c) fusing said cells of each spleen of step (b) with animal myeloma cells in the presence of a fusion promoter;

(d) diluting and culturing the fused cells from step (c) in separate wells in a medium which will not support the unfused myeloma cells;

(e) evaluating the supernatant in each well containing a hybridoma for the presence of antibodies to fibrin II, (T)N-DSK, or any related fragments thereof;

(f) selecting and cloning a hybridoma which produces antibody which reacts with a peptide fragment of the Bβ chain of human fibrin II containing amino acid residues 15-42, but does not react with either of the peptide fragments of the Bβ chain of fibrinogen or fibrin I containing only amino acid residues 1-14 or 1-42; and (g) recovering the antibody from the supernatant of said clones.

35. A monoclonal antibody according to claim 34, wherein said animal is a mouse.

36. A monoclonal antibody according to claim 11, wherein said antibody is prepared by the method, which comprises the steps of:

(a) immunizing an animal with a homogeneous solution consisting essentially of (T)N-DSK;

(b) removing the spleen from each animal of step (a) and making a suspension of the cells from each spleen;

(c) fusing said cells of each spleen of step (b) with animal myeloma cells in the presence of a fusion promoter;

(d) diluting and culturing the fused cells from step (c) in separate wells in a medium which will not support the unfused myeloma cells; and (e) evaluating the supernatant in each well containing a hybridoma for the presence of antibodies to fibrin II, (T)N-DSK, or any related fragment thereof;

(f) selecting and cloning a hybridoma which produces antibody which reacts with a peptide fragment of the BB chain of human fibrin II containing amino acid residues 15-42, but does not react with either of the peptide fragments of the BB chain of fibrinogen or fibrin I containing amino acid residues 1-14 or 1-42;

(g) transferring said clones intraperitoneally into mice; and (h) harvesting the malignant ascites or serum from said mice, which ascites the serum contains the desired antibody.

37. A monoclonal antibody according to claim 36, wherein said animal is a mouse.

38. A method of preparing a monoclonal antibody wherein said antibody:

(i) reacts with a peptide fragment of the Bβ chain of human fibrin II containing amino acid residues 15-42 of said Bβ chain;

(ii) does not react with a peptide fragment of the Bβ chain of human fibrinogen or fibrin I containing amino acid residues 1-14; and (iii) does not react with a peptide fragment of the Bβ chain of human fibrinogen or fibrin I containing amino acid residues 1-42, said method comprising the steps of:

(a) immunizing an animal with a solution comprising (T)N-DSK;

(b) removing the spleen from each animal of step (a) and making a suspension of the cells from each spleen;

(c) fusing said cells of each spleen of step (b) with animal myeloma cells in the presence of a fusion promoter;

(d) diluting and culturing the fused cells from step (c) in separate wells in a medium which will not support the unfused myeloma cells;

(e) evaluating the supernatant in each well containing a hybridoma for the presence of antibodies to fibrin II, (T)N-DSK, or any related fragments thereof, (f) selecting and cloning a hybridoma producing antibody which reacts with the peptide fragment of the Bβ chain of human fibrin II containing amino acid residues 15-42, but does not react with either of the peptide fragments of the Bβ chain of fibrinogen or fibrin I containing amino acid residues 1-14 or 1-42.

(g) transferring said clones intraperitoneally into animals; and (h) harvesting the malignant ascites or serum from said animals, which ascites or serum contains the desired antibody.

39. A method of preparing a monoclonal antibody according to claim 38, wherein said animal is a mouse.

40. A method of preparing a monoclonal antibody wherein said antibody:

(i) reacts with a peptide fragment of the Bβ chain of human fibrin II containing amino acid residues 15-42 of said Bβ chain;

(ii) does not react with a peptide fragment of the Bβ chain of human fibrinogen or fibrin I containing amino acid residues 1-14; and (iii) does not react with a peptide fragment of the Bβ chain of human fibrinogen or fibrin I containing amino acid residues 1-42, said method comprising the steps of:

(a) immunizing an animal with a homogeneous solution consisting essentially of (T)N-DSK;

(b) removing the spleen from each animal of step (a) and making a suspension of the cells from each spleen;

(c) fusing said cells of each spleen of step (b) with animal myeloma cells in the presence of a fusion promoter;

(d) diluting and culturing the fused cells from step (b) in separate wells in a medium which will not support the unfused myeloma cells;

(e) evaluating the supernatant in each well containing a hybridoma for the presence of antibodies to fibrin II or any related fragments thereof;

(f) selecting and cloning a hybridoma which produces antibody which reacts with a peptide fragment of the Bβ chain of human fibrin II containing amino acid residues 15-42 but does not react with either of the peptide fragments of the Bβ chain of fibrinogen or fibrin I containing amino acid residues 1-14 or 1-42; and (g) recovering the antibody from the supernatant of said clones.

41. A method of preparing a monoclonal antibody according to claim 40 wherein said animal is a mouse.

* * * * *

UNITED STATES PATENT AND TRADEMARK OFFICE
CERTIFICATE OF CORRECTION

PATENT NO. : 4,851,334

DATED : July 25, 1989

INVENTOR(S) : Bohdan J. Kudryk, et al

Page 1 of 2

It is certified that error appears in the above-identified patent and that said Letters Patent is hereby corrected as shown below:

| | |
|---|---|
| Title Page, Page 2, line 2 under "Other Publications" | Delete "Elms" second instance |
| Col. 1, line 9 | After "application" delete "--" |
| Col. 1, line 15 | Before "Fibrin" delete "at" and substitute --or-- |
| Col. 1, line 18 | Correct spelling of --hybridomas-- |
| Col. 1, line 40 | Correct spelling of --Haemostas.-- |
| Col. 1, line 65 | Delete "1983" and substitute --1973-- |
| Col. 2, line 53 | After "FPA" delete "an" and substitute --and-- |
| Col. 6, line 38 | After "Accordingly," delete "the" and substitute --in-- |
| Col. 12, line 7 | Delete "and" and substitute --or-- |
| Col. 13, line 48 | After "provided" insert --. An aliquot (e.g., 2-4 mg) of fibrin is also provided-- |
| Col. 15, line 15 | Delete "5804" and substitute --5806-- |
| Col. 17, line 57 | After "10%" insert --NCTC 109-- |
| Col. 21, line 62 | Delete "an" and substitute --and-- |
| Col. 22, line 63 | Correct --concentration-- |
| Col. 22, line 65 | Correct --higher-- |
| Col. 24, line 41 | Correct --earlier-- |
| Col. 25, line 18 | Delete "cold" and substitute --could-- |
| Col. 25, line 66 | Delete "antigen" |
| Col. 26, line 33 | Delete "wih" and substitute --with-- |

UNITED STATES PATENT AND TRADEMARK OFFICE
CERTIFICATE OF CORRECTION

PATENT NO. : 4,851,334

DATED : July 25, 1989

INVENTOR(S) : Bohdan J. Kudryk, et al

It is certified that error appears in the above-identified patent and that said Letters Patent is hereby corrected as shown below:

Col. 26, line 42      Delete "resides" and substitute --residues--

Col. 27, line 16      Delete "humam" and substitute --human--

Col. 32, line 58      Delete "claim 11" and substitute --claim 1--

Col. 34, line 60      Delete "claim 123" and substitute --claim 32--

Signed and Sealed this

Twelfth Day of February, 1991

Attest:

HARRY F. MANBECK, JR.

*Attesting Officer*      *Commissioner of Patents and Trademarks*